(12) United States Patent
Erickson et al.

(10) Patent No.: US 7,109,230 B2
(45) Date of Patent: Sep. 19, 2006

(54) RESISTANCE-REPELLENT RETROVIRAL PROTEASE INHIBITORS

(75) Inventors: John W. Erickson, Frederick, MD (US); Michael Eissenstat, Frederick, MD (US); Abelardo Silva, Columbia, MD (US); Sergei Gulnik, Frederick, MD (US)

(73) Assignee: Sequoia Pharmaceuticals, Inc., Gaithersburg, MD (US)

( * ) Notice: Subject to any disclaimer, the term of this patent is extended or adjusted under 35 U.S.C. 154(b) by 223 days.

(21) Appl. No.: 10/337,349

(22) Filed: Jan. 7, 2003

(65) Prior Publication Data

US 2003/0171423 A1 Sep. 11, 2003

Related U.S. Application Data

(60) Provisional application No. 60/344,788, filed on Jan. 7, 2002, and provisional application No. 60/383,575, filed on May 29, 2002.

(51) Int. Cl.
*A61K 31/40* (2006.01)
*C07D 209/36* (2006.01)

(52) U.S. Cl. ........................................ 514/412; 548/484
(58) Field of Classification Search ................ 514/412; 548/484
See application file for complete search history.

(56) References Cited

U.S. PATENT DOCUMENTS

| | | |
|---|---|---|
| 5,856,353 A | 1/1999 | Tung et al. |
| 5,990,155 A | 11/1999 | Tung et al. |
| 6,060,476 A | 5/2000 | Vazquez et al. |
| 6,172,082 B1 | 1/2001 | Vazquez et al. |
| 6,248,775 B1 | 6/2001 | Vazquez et al. |
| 6,319,946 B1 | 11/2001 | Hale et al. |
| 6,335,460 B1 | 1/2002 | Vazquez et al. |
| 6,392,046 B1 | 5/2002 | Tung et al. |
| 6,417,387 B1 | 7/2002 | Vazguez et al. |
| 6,455,581 B1 | 9/2002 | Vazquez et al. |
| 6,500,832 B1 | 12/2002 | Vazquez et al. |
| 6,534,493 B1 | 3/2003 | Vazquez et al. |
| 2002/0049201 A1 | 4/2002 | Hale et al. |
| 2002/0052399 A1 | 5/2002 | Vazquez et al. |
| 2003/0069222 A1 | 4/2003 | Tung et al. |

FOREIGN PATENT DOCUMENTS

| | | |
|---|---|---|
| WO | WO 99/67417 | 12/1999 |
| WO | WO 02/081478 A2 | 10/2002 |
| WO | WO 02/083657 A2 | 10/2002 |
| WO | WO 02/092595 A1 | 11/2002 |

*Primary Examiner*—Kamal A. Saeed
(74) *Attorney, Agent, or Firm*—Heller Ehrman LLP

(57) ABSTRACT

Resistance-repellent and multidrug resistant retroviral protease inhibitors are provided. Pharmaceutical composition comprising such compounds, and methods of using such compounds to treat HIV infections in mammals, are also provided.

26 Claims, 8 Drawing Sheets

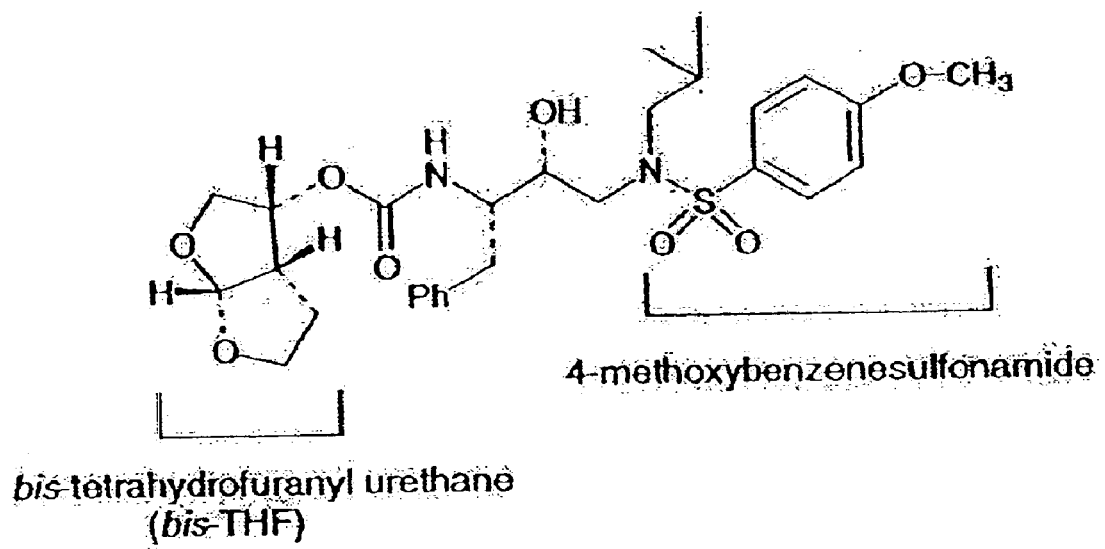
FIG. 1. Structure of UIC-94003.

FIG. 2. In vitro selection of HIV-1 variants resistant to UIC-94003 and amprenavir. A laboratory HIV-1 strain, HIV-1$_{NL4-3}$, was passaged in the presence of increasing concentrations of UIC-94003 (○) or amprenavir (●) in MT-2 cells. The selection was carried out in a cell-free manner for a total of 34 to 64 passages with drug concentrations escalating from 0.0005 to 10 μM. Nucleotide sequences of proviral DNA were determined using cell lysates of HIV-1-infected MT-2 cells at the termination of each indicated passage.

FIG. 3. Sequence analysis of the protease-encoding region of HIV-1 passaged in the presence of UIC-94003. The amino acid sequences of protease deduced from nucleotide sequences of the protease-encoding region of HIV-1 clones determined at nine different passages are illustrated. The fraction of clones examined is indicated on the right. The amino acid sequence of protease of a wild-type pNL4-3 clone is shown as a reference. Identity with this sequence at individual amino acid positions is indicated (dots).

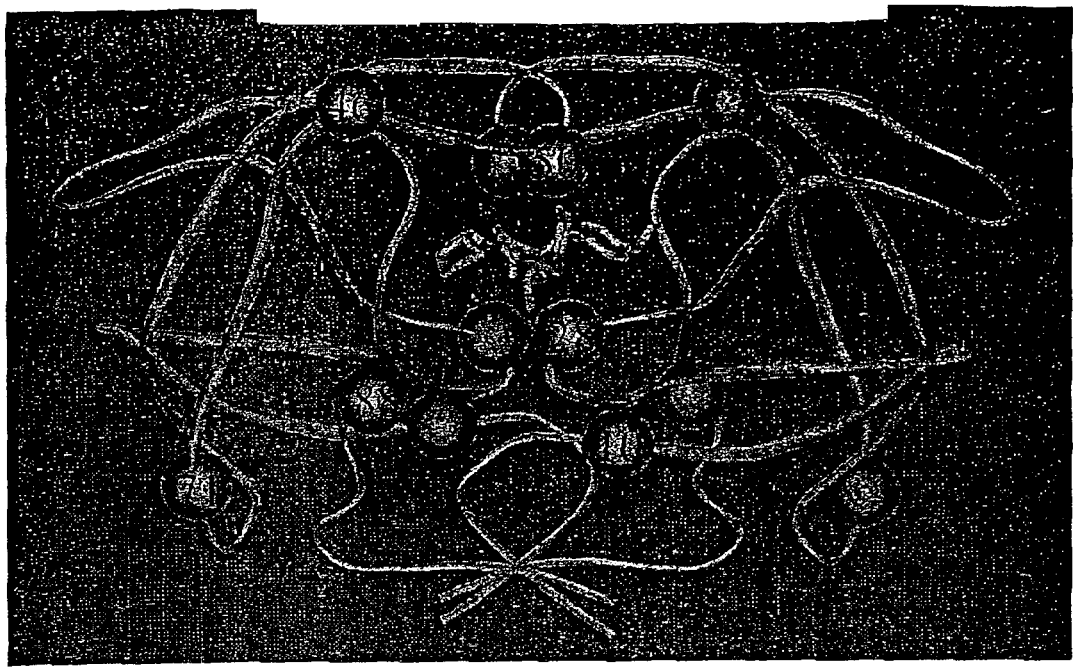

FIG. 4. Backbone diagram of the dimeric HIV-1 protease. A model of UIC-94003 bound in the active site is shown in stick lines. The six residues which are commonly mutated during in vitro selection with UIC-94003 are indicated by spheres. Two of these residues lie within the active site (residues 28 and 50), while the other four residues lie outside the active site (residues 10, 46, 71, and 88).

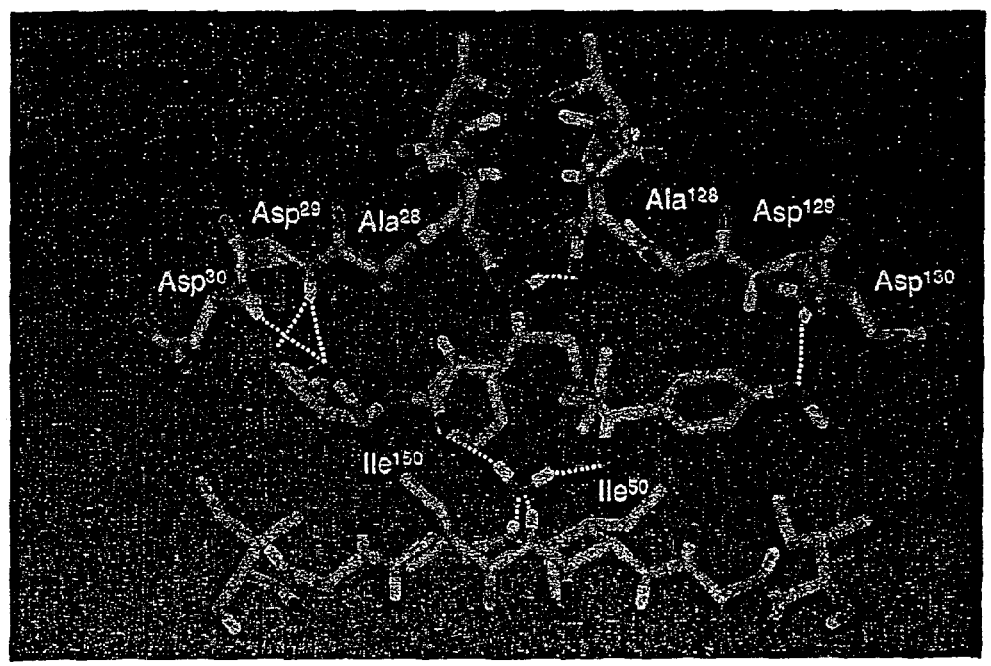

FIG. 5. Modeling of UIC-94003 bound in the active site of HIV-1 protease. Hydrogen bonds are represented as dotted lines.

Figure 6:
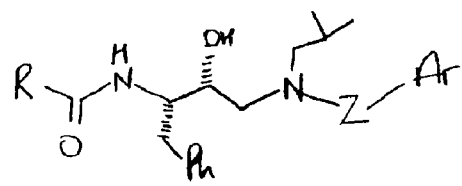
where:
R = 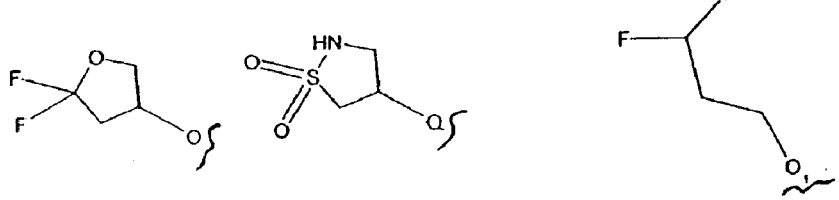
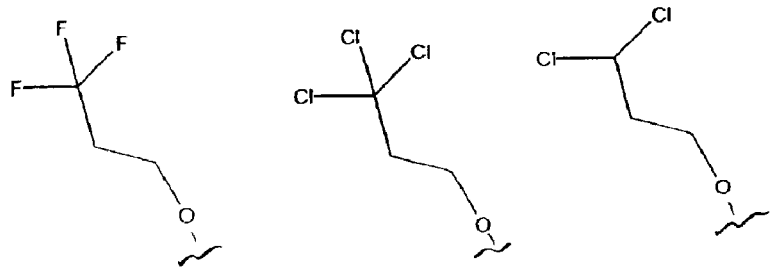
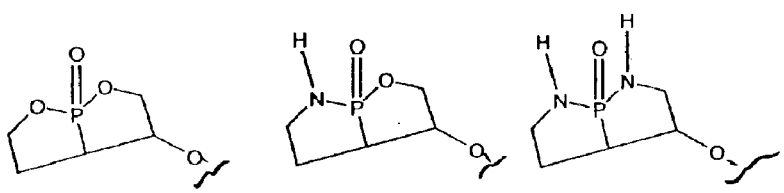
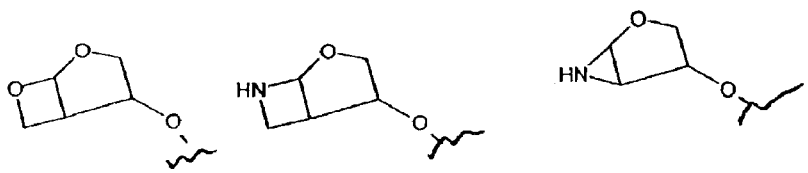
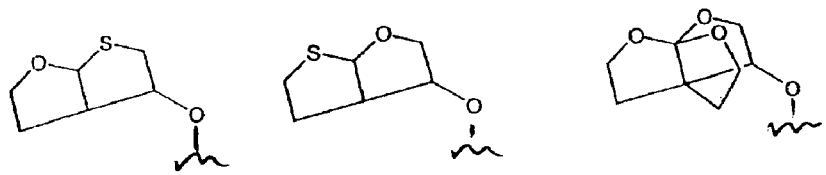
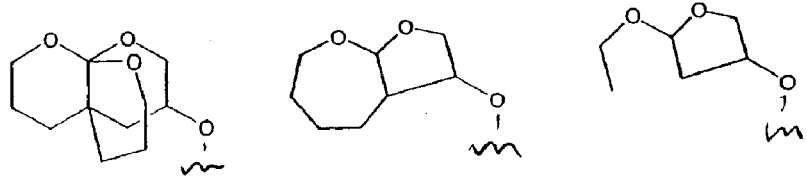

Figure 6 (continued):

where Z is, for example, –S(O)$_2$-, -C(O)-, -C(O)-NH-, or -C(O)-O-, and where Ar is, for example, 4-methoxyphenyl, 4-aminophenyl, phenyl, 4-methylaminophenyl, or 4-pyridyl

Figure 7

Table 8

| Atom | x [Å] | y [Å] | z [Å] | σ [Å] | Description |
|---|---|---|---|---|---|
| Substructure of the protein | | | | | |
| O301 | -7.9 | 13.6 | 27.4 | 0.5 | Oxygen atom of water molecule coordinated to main chain amide nitrogen atoms of amino acid Gly 49 and Gly149 |
| O27 | -13.8 | 17.7 | 30.4 | 0.5 | Main Chain carbonyl oxygen atom of amino acid Gly 27 |
| N29 | -13.4 | 18.2 | 34.5 | 0.5 | Main chain amide nitrogen atom of amino acid Asp 29 |
| N30 | -11.9 | 18.6 | 36.7 | 0.5 | Main chain amide nitrogen atom of amino acid Asp 30 |
| OD1 25 | -11.3 | 21.2 | 28.7 | 0.5 | Carboxylate oxygen atom of aminoacid Asp 25 |
| OD2 25 | -9.4 | 20.4 | 29.3 | 0.5 | Carboxylate oxygen atom of aminoacid Asp 25 |
| OD1 125 | -12.7 | 20.3 | 26.4 | 0.5 | Carboxylate oxygen atom of aminoacid Asp 125 |
| OD2 125 | -12.7 | 20.3 | 26.4 | 0.5 | Carboxylate oxygen atom of aminoacid Asp 125 |
| N129 | -8.9 | 20.5 | 20.7 | 0.5 | Main chain amide nitrogen atom of amino acid Asp 129 |
| N130 | -10.1 | 19.5 | 18.6 | 0.5 | Main chain amide nitrogen atom of amino acid Asp 130 |
| Substructure of the inhibitor | | | | | |
| HD:A | -8.8 | 17.5 | 25.7 | 0.5 | Interacting with main chain carbonyl oxygen |

| | | | | | |
|---|---|---|---|---|---|
| | | | | | atom of amino acid Gly 27 |
| HA:A | -8.5 | 15.3 | 25.1 | 0.5 | Interacting with Oxygen atom of water molecule coordinated to main chain amide nitrogen atoms of amino acid Gly 49 and Gly149 |
| HD/A:B | -10.4 | 19.1 | 27.4 | 0.5 | Interacting with carboxylate oxygen atoms of aminoacids Asp 25 and Asp 125 |
| HA:A' | -8.9 | 14.0 | 29.8 | 0.5 | Interacting with Oxygen atom of water molecule coordinated to main chain amide nitrogen atoms of amino acid Gly 49 and Gly149 |
| HA1:X | -8.6 | 17.3 | 20.7 | 0.5 | Main chain amide nitrogen atom of amino acid Asp 30 |
| HA2:X | -6.9 | 18.7 | 21.4 | 0.5 | Interacting with main chain amide nitrogen atom of amino acid Asp 29 |
| HA:X' | -10.7 | 15.8 | 35.8 | 0.5 | Interacting with main chain amide nitrogen atom of amino acid Asp 130 |

Figure 7 (Continued)

RESISTANCE-REPELLENT RETROVIRAL PROTEASE INHIBITORS

This application claims priority under 35 USC § 119 to application Ser. Nos. 60/344,788, filed Jan. 7, 2002, and 60/383,575, filed May 29, 2002, the specifications of which are incorporated herein by reference in their entirety.

The present invention relates to retroviral protease inhibitors and, more particularly, relates to novel compounds, compositions and methods for inhibiting retroviral proteases. This invention, in particular, relates to resistance-repellent HIV protease inhibitors, compositions, and uses thereof for treating HIV infections, particularly infections caused by one or more species of drug resistant HIV strains.

BACKGROUND OF THE INVENTION

Acquired immune deficiency syndrome (AIDS) is a fatal disease, reported cases of which have increased dramatically within the past several years. Estimates of reported cases in the very near future also continue to rise dramatically. Consequently, there is a great need to develop drugs and vaccines to combat AIDS.

The AIDS virus was first identified in 1983. It has been known by several names and acronyms. It is the third known T-lymphocyte virus (HTLV-III), and it has the capacity to replicate within cells of the immune system, causing profound cell destruction. The AIDS virus is a retrovirus, a virus that uses reverse transcriptase during replication. This particular retrovirus is also known as lymphadenopathy-associated virus (LAV), AIDS-related virus (ARV) and, most recently, as human immunodeficiency virus (HIV). Two distinct families of HIV have been described to date, namely HIV-1 and HIV-2. The acronym HIV is used hereinafter to refer to HIV viruses generically.

Specifically, HIV is known to exert a profound cytopathic effect on CD4+ helper/inducer T-cells, thereby severely compromising the immune system. HIV infection also results in neurological deterioration and, ultimately, in the death of the infected individual.

The field of viral chemotherapeutics has developed in response to the need for agents effective against retroviruses, in particular HIV. Theoretically, there are many ways in which an agent can exhibit anti-retroviral activity. The HIV genome encodes several viral-specific enzymes, such as reverse transcriptase (RT), integrase and protease (PR); viral-specific regulatory proteins, such as tat, rev, nef and vif; and, numerous viral-specific structural proteins, and numerous viral-specific structural proteins, such as capsid, nucleocapsid, matrix, and envelope proteins. Many of these proteins are essential for viral replication. Accordingly, viral replication theoretically could be inhibited through inhibition of any one or all of the proteins involved in viral replication. In practice, however, only inhibitors of RT and PR are currently available for antiviral therapy.

Nucleoside analogues (NRTIs), such as 3'-azido-2',3'-dideoxythymidine (AZT), 2',3'-dideoxycytidine (ddC), and 2',3'-dideoxyinosine (ddI) are known to inhibit HIV RT. There also exist non-nucleoside inhibitors (NNRTIs) specific for HIV-1 RT, such as Nevirapine, and Efavirenz.

Retroviral PR inhibitors (PIs) have also been identified as a class of anti-retroviral agents. The retroviral PR processes polyprotein precursors into viral structural proteins and replicative enzymes. This processing is essential for the assembly and maturation of fully infectious virions. Accordingly, the design of PIs that selectively inhibit PR has been an important therapeutic goal in the treatment of HIV infections and AIDS. Strategies used in the design of HIV PIs include substrate-based, peptidomimetic, transition state-based, and structure-based drug design (Wlodawer & Erickson, *Ann. Rev. Biochem.*, 62, 543–585 (1992)).

Numerous classes of potent peptidic inhibitors of PR have been designed using the natural cleavage site of the precursor polyproteins as a starting point. These inhibitors typically are peptide substrate analogs in which the scissile P1–P1' amide bond has been replaced by a non-hydrolyzable isostere with tetrahedral geometry (Moore et al., *Perspect. Drug Dis. Design*, 1, 85 (1993); Tomaselli et al., *Int. J. Chem. Biotechnology*, 6 (1991); Huff, *J. Med. Chem.*, 34, 2305 (1991); Norbeck et al., *Ann. Reports Med. Chem.*, 26, 141 (1991); Meek, *J. Enzyme Inhibition*, 6, 65 (1992)).

The design of HIV-1 PIs based on the transition-state mimetic concept has led to the generation of a variety of peptide derivatives highly active against viral replication in vitro (Erickson et al., *Science;* 249, 527–533 (1990); Kramer et al., *Science,* 231, 1580–1584 (1986); McQuade et al., *Science,* 247, 454–456 (1990); Meek et al., *Nature (London),* 343, 90–92 (1990); Roberts et al., *Science,* 248, 358–361 (1990)). These active agents contain a non-hydrolyzable, dipeptide isostere such as hydroxyethylene (McQuade et al., supra; Meek et al., *Nature (London),* 343, 90–92 (1990); Vacca et al., *J. Med. Chem.,* 34, 1225–1228 (1991)) or hydroxyethylamine (Rich et al., *J. Med. Chem.,* 33, 1285–1288 (1990); Roberts et al., *Science,* 248, 358–361 (1990)) as an active moiety which mimics the putative transition state of the aspartic protease-catalyzed reaction.

Two-fold (C2) symmetric inhibitors of HIV protease represent another class of potent HIV PIs which were created by Erickson et al. on the basis of the three-dimensional symmetry of the enzyme active site (Erickson et al., supra).

Typically, the usefulness of currently available HIV PIs in the treatment of AIDS has been limited by relatively short plasma half-life, poor oral bioavailability, and the technical difficulty of scale-up synthesis (Meek et al. (1992), supra). Although these inhibitors are effective in preventing the retroviral PR from functioning, the inhibitors suffer from some distinct disadvantages. Generally, peptidomimetics make poor drugs due to their potential adverse pharmacological properties, i.e., poor oral absorption, poor stability and rapid metabolism (Plattner et al., Drug Discovery Technologies, Clark et al., eds., Ellish Horwood, Chichester, England (1990)). Furthermore, since the active site of the PR is hindered, i.e., has reduced accessibility as compared to the remainder of the PR, the ability of the inhibitors to access and bind in the active site of the PR is impaired. Those inhibitors that do bind are generally poorly water-soluble, causing distinct problems for formulation and drug delivery.

There are currently six FDA-approved PIs for clinical use—Saquinavir, Ritonavir, Indinavir, Nelfinavir, Amprenavir and Lopinavir. When used alone or in combination with RT inhibitors, PIs dramatically suppress viral replication in HIV-infected individuals. Accordingly, PIs have become "first-line" antiviral agents for the control of HIV-1 (HIV) infections and are widely used in most highly active anti-retroviral therapy (HAART) regimens (Boden & Markowitz, *Antimicrob. Agents Chemo.,* 42, 2775–2783, (1998)). Despite their success, the widespread use of PIs has led to the emergence of several thousands of genetically distinct, drug resistant HIV variants, many of which are cross-resistant to the PIs as a class (Richman, *Adv. Exp. Med. Biol.,* 392, 383–395 (1996); Boden & Markowitz (1998), supra; Shafer et al. *Ann. Intern. Med.,* 128, 906–911(1998)).

The ability of HAART to provide effective long-term antiretroviral therapy for HIV-1 infection has become a complex issue since 40 to 50% of those who initially achieve favorable viral suppression to undetectable levels experience treatment failure (Grabar et al., *AIDS,* 14, 141–149 (1999); Wit et al., *J. Infect. Dis.,* 179, 790–798 (1999)). Moreover, 10 to 40% of antiviral therapy-naive individuals infected with HIV-1 have persistent viral replication (plasma HIV RNA >500 copies/ml) under HAART (Gulick et al., *N. Engl. J. Med.,* 337, 734–739 (1997); Staszewski et al., *N. Engl. J. Med.,* 341, 1865–1873 (1999)), possibly due to transmission of drug-resistant HIV-1 variants (Wainberg and Friedland, *JAMA,* 279, 1977–1983 (1998)). In addition, it is evident that with these anti-HIV drugs only partial immunologic reconstitution is attained in patients with advanced HIV-1 infection.

The clinical manifestations of drug resistance are viral RNA rebound and decreased CD4 cell-counts in the continued presence of drug. The majority of clinical resistance cases are due to viral adaptation through the generation and selection of mutations in the PR and RT genes. Mutant viruses can be generated through errors in reverse transcription of viral RNA, viral RNA synthesis, and recombination events (Coffin, *Retroviruses* pp. 143–144, Cold Spring Harbor Laboratory Press, Plainview (1997)). Mutations within the protease gene that confer clinical drug resistance have emerged for all of the FDA-approved HIV PR inhibitors. The rapid development of drug resistance to PIs, combined with the transmissibility of drug-resistant HIV strains to newly-infected individuals, has resulted in the emergence of a new epidemic of multi-drug resistant AIDS (mdrAIDS). Multi-drug resistant AIDS is caused by a complex spectrum of genetically distinct, infectious new HIV strains that resist most or all forms of currently available treatment.

Accordingly, drug resistant HIV strains represent distinct infectious entities from a therapeutic viewpoint, and pose new challenges for drug design as well as drug treatment of existing infections. Substitutions have been documented in over 45 of the 99 amino acids of the HIV protease monomer in response to protease inhibitor treatment (Mellors, et al., *International Antiviral News,* 3, 8–13(1995); Eastman, et al., *J. Virol.,* 72, 5154–5164(1998); Kozal, et al., *Nat. Med.,* 2, 753–759(1996)). The particular sequence and pattern of mutations selected by PIs is believed to be somewhat drug-specific and often patient-specific, but high level resistance is typified by multiple mutations in the protease gene which give rise to cross-resistance to all of the PIs.

The challenge of tackling drug resistance is perhaps best illustrated by considering the dynamics of a typical HIV infection. Approximately $10^{12}$ virions are produced in an HIV infected individual every day. The mutation rate of HIV is approximately 1 per genome, which numbers $10^4$ nucleotide bases. Therefore, every nucleotide in the genome is mutated $10^8$ times per round of replication in the patient. This means that all possible single site mutations are present in at least the 0.01% level. Because of this, drugs that can be rendered ineffective with a single mutation from wild type have the shortest effective lifetime in monotherapy settings. The apparently large number of possible mutational pathways, possible mutational combinations, and the danger of generating class-specific cross resistance can make the choice of a subsequent protease inhibitor-containing combination regimen for "salvage therapy" seem very complicated and risky. Even the choice of protease inhibitor with which to initiate therapy, so-called "first-line" therapy, can be a risky enterprise that may inadvertently select for an undesired resistance pathway. Drug-naive HIV-infected individuals pose even more of a risk for developing resistance to first-line therapies.

For the reasons outlined above, the development of new anti-HIV-1 therapeutics presents formidable challenges different from those in the design of the first line drugs, particularly in regard to consideration of selection pressure mechanisms in addition to the conventional issues of potency, pharmacology, safety, and mechanism of drug action. Indeed, HIV-1 can apparently develop resistance to any existing anti-HIV-1 therapeutic. In particular, the very features that contribute to the specificity and efficacy of RTIs and PIs provide the virus with a strategy to mount resistance (Erickson and Burt, *Annu. Rev. Pharmacol. Toxicol.,* 36, 545–571 (1996); Mitsuya and Erickson, *Textbook of AIDS Medicine,* pp. 751–780, Williams and Wilkins, Baltimore (1999)), and it seems highly likely that this resistance issue will remain problematic for years to come.

Despite numerous studies of drug resistance to PIs, successful strategies to design inhibitors directly targeted against drug resistant HIV have been lacking. Instead, efforts have been directed at identifying drugs with increased potency to wild type virus, and with longer pharmacological half-lives (exemplified by Amprenavir). Another approach has been to develop PIs that are sensitive to pharmacologic "boosting" using Ritonavir, a PI that is also a potent inhibitor of the cytochrome enzymes. The latter approach, exemplified by Kaletra (a Lopinavir/Ritonavir combination), involves higher total drug exposures to PIs which, over time, may lead to long term, serious side effects. Several other PIs have been identified based on efforts to improve plasma half-life and bioavailability. For example, PIs incorporating the 2,5-diamino-3,4-disubstituted-1,6-diphenylhexane isostere are described in Ghosh et. al., *Bioorg. Med. Chem. Lett.,* 8, 687–690 (1998) and U.S. Pat. No. 5,728,718 (Randad et al.), both of which are incorporated herein by reference in their entirety. HIV PIs, which incorporate the hydroxyethylamine isostere, are described in U.S. Pat. No. 5,502,060 (Thompson et al.), U.S. Pat. No. 5,703,076 (Talley et al.), and U.S. Pat. No. 5,475,027 (Talley et al.).

Recent studies have revealed the structural and biochemical mechanisms by which mutations in the PR gene of HIV confer drug resistance in the presence of PIs. An important conclusion that emerges from the body of evidence on resistance to PIs is that HIV variants that exhibit cross-resistance to first-line PIs should be considered to be unique infectious agents. New therapeutic agents need to be developed to successfully treat patients infected with these viruses. New strategies for drug discovery need to be explored to develop effective protease inhibitor-based treatments for patients with multidrug resistant virus. HIV protease is one the most intensively studied molecular targets in the history of infectious disease.

More recently, new mutant strains of HIV have emerged that are resistant to multiple, structurally diverse, experimental and chemotherapeutic HIV PIs. Such mdrHIV strains are typically found in infected patients who have undergone treatment with a combination of PIs or with a series of different PIs. The number of reported cases of patients infected with mdrHIV is rising steadily. Tragically for these patients, the available options for AIDS chemotherapy and/or HIV management is severely limited or is, otherwise, completely nonexistent.

A biochemical fitness profiling strategy has recently been used to identify a novel subclass of potent PIs that have broad-based activity against mdrHIV (Gulnik et al., (1995) supra; Erickson et al., WO 99/67254; Erickson et al., WO 99/67417).

In view of the foregoing problems, there exists a need for inhibitors against drug resistant and mdrHIV strains. Further, there exists a need for inhibitors against drug resistant and multi-drug resistant HIV proteases (mdrPR). Further still, there exists a need for inhibitors of HIV that can prevent or slow the emergence of drug resistant and mdrHIV strains in infected individuals. Inhibitors with the ability to inhibit mdrHIV strains, and to slow the emergence of drug resistant strains in wild type HIV infections, are defined as "resistance-repellent" inhibitors. There also exists a need for robust methods that can be used to design "resistance-repellent" inhibitors.

SUMMARY OF THE INVENTION

The present invention provides such resistance-repellent inhibitors of mdrPR, their compositions, methods of design, and uses thereof for treating mdrHIV and wtHIV infections in salvage therapy and first-line therapy modalities.

More particularly, the invention provides HIV protease inhibitors represented by the formula I:

                                            I where X is a moiety that contains two or more hydrogen bond acceptors capable of interacting with the backbone NH atoms of residues 29 and 30 of an HIV protease, A is a 2–6 atom linker that contains at least one hydrogen bond acceptor that interacts with the flap water, and one hydrogen bond donor that interacts with the backbone CO atom of residue 27, B contains 1–3 atoms that can form hydrogen bonds with either or both carboxylate side chain oxygens of Asp25 and Asp 125 of said protease, A' is a 2–6 atom linker that contains at least one hydrogen bond acceptor that interacts with the flap water; and X' is a moiety that can form one or more hydrogen bonds with the backbone NH atoms of residues 129 and/or 130, provided that the compound of Formula I is not any of the compounds described in *J. Med. Chem.* 39:3278–3290 (1996), in *Bioorg. Med. Chem. Lett.* 8:687–690 (1998), or *Bioorg. Med. Chem. Lett.* 8:979–982 (1998).

The invention also provides a compound as described above, bound in a complex with wild type or drug resistant mutant forms of HIV-1 protease.

The invention further provides pharmaceutical compositions, comprising an inhibitor as described above, together with a pharmaceutically acceptable additive, excipient, or diluent. The composition may further comprise an additional HIV protease inhibitor and/or an HIV reverse transcriptase inhibitor.

The invention further provides methods of treating a patient suffering from HIV infection, comprising administering to the patient a pharmaceutical composition as described above.

BRIEF DESCRIPTION OF THE DRAWINGS

FIG. 1 shows the structure of 1.

FIG. 2 shows in vitro selection of HIV-1 variants resistant to 1 and amprenavir. A laboratory HIV-1 strain, HIV-1$_{NL4-3}$, was passaged in the presence of increasing concentrations of 1 (○) or amprenavir (●) in MT-2 cells. The selection was carried out in a cell-free manner for a total of 34–64 passages with drug concentrations escalating from 0.0005 to 10 μM. Nucleotide sequences of proviral DNA were determined using cell lysates of HIV-1-infected MT-2 cells at the termination of each indicated passage.

FIG. 3 shows sequence analysis of the protease-encoding region of HIV-1 passaged in the presence of 1. The amino acid sequences of protease deduced from nucleotide sequences of the protease-encoding region of HIV-1 clones determined at nine different passages are illustrated. The fraction of clones examined is indicated on the right. The amino acid sequence of protease of a wild-type pNL4-3 clone is shown as a reference. Identity with this sequence at individual amino acid positions is indicated by dots.

FIG. 4 shows a backbone diagram of the dimeric HIV-1 protease. A model of 1 bound in the active site is shown in stick lines. The six residues which are commonly mutated during in vitro selection with 1 are indicated by spheres. Two of these residues lie within the active site (residue 28 and 50), while the other four residues lie outside of the active site (residue 10, 46, 71 and 88).

FIG. 5 shows modeling of 1 bound in the active site of HIV-1 protease. Hydrogen bonds are represented as dotted lines.

FIG. 6 shows the structures of some compounds of general formula I.

FIG. 7 shows a set of three-dimensionally-conserved substructures of an HIV protease substrate binding site and the substructure of atoms of an inhibitor interacting with the conserved substructure of the protease.

Table 1 shows the sensitivities of three HIV strains to various HIV drugs.

Table 2 shows the PI sensitivities of HIV strains isolated from heavily-drug experienced individuals.

Table 3 shows amino acid substitutions in PR and sensitivities of drug-resistant HIV-1 strains to protease inhibitors.

DETAILED DESCRIPTION OF THE PREFERRED EMBODIMENTS

The invention provides 'resistance-repellent' retroviral protease inhibitors. A 'resistance-repellent' protease inhibitor ("PI") is a compound that retains inhibitory activity, or potency, over a broad spectrum of related but non-identical retroviral proteases. Examples of resistance-repellent PIs include, but are not limited to, PIs that inhibit wild type HIV-1 protease derived from any clade B virus and 1) a wild type retroviral protease from one or more different retroviruses, such as HIV-2 protease; or 2) mutant HIV-1 proteases with single active site mutations at residues 30, 82 and 84; or 3) mutant HIV-1 proteases with single active site mutations at residues 47, 48, and 50; or 4) mutant HIV-1 proteases with double active site mutations at residues 82 and 84; or 5) mutant HIV-1 proteases with double active site mutations at residues 47 and 48, 47 and 50, or 48 and 50; or 6) mutant HIV-1 proteases with double active site mutations at residues 48 and 82, 48 and 90, or 82 and 90; or 7) mutant HIV-1 proteases with three or more active site mutations in any combination at residues 32, 47, 48, 50, 82, 84 or 90.

The term "pharmaceutically effective amount" refers to an amount effective in treating a virus infection, for example an HIV infection, in a patient either as monotherapy or in combination with other agents. The term "treating" as used herein refers to the alleviation of symptoms of a particular disorder in a patient or the improvement of an ascertainable measurement associated with a particular disorder. The term "prophylactically effective amount" refers to an amount effective in preventing a virus infection, for example an HIV infection, in a patient. As used herein, the term "patient" refers to a mammal, including a human.

The applicants have found that compounds having the general formula I are effective against a wide variety of PI-resistant HIV strains

X-A-B-A'-X'        I where X is a moiety that contains two or more hydrogen bond acceptors capable of interacting with the backbone NH atoms of residues 29 and 30 of an HIV protease, A is a 2–6 atom linker that contains at least one hydrogen bond acceptor that interacts with the flap water, and one hydrogen bond donor that interacts with the backbone CO atom of residue 27, B contains 1–3 atoms that can form hydrogen bonds with either or both carboxylate side chain oxygens of Asp25 and Asp 125 of said protease, A' is a 2–6 atom linker that contains at least one hydrogen bond acceptor that interacts with the flap water; and X' is a moiety that can form one or more hydrogen bonds with the backbone NH atoms of residues 129 and/or 130. Some compounds conforming to this general formula have been described and the present invention specifically excludes those compounds.

Resistance-repellent PIs should generally also retain inhibitory activity, or potency, over a broad spectrum of related but non-identical retroviruses. In particular, resistance-repellent PIs should inhibit all HIV-1 virus strains that contain a gene sequence of the protease region of the HIV-1 pol gene that is typified by one or more 'wild type' strains derived from clade B and: 1) HIV-1 virus strains that contain a gene sequence of the protease region of the HIV-1 pol gene derived from wild type, non-clade B viruses; or 2) wild type HIV-2 virus strains; or 3) HIV-1 virus strains derived from patients who are infected with HIV-1 that contain mutations in the protease gene.

Comparative analysis of the x-ray crystal structures of complexes of different inhibitors bound to wild type and mutant forms of HIV protease has led the applicants to the insight that a substructure in the active site of HIV protease is structurally-conserved. It has also been discovered that compositions that form selective interactions with this conserved substructure, have attributes of resistance-repellent inhibitors of HIV protease. This insight has not been previously described. These insights have led the applicants to design improved HIV PI compounds that are effective against multidrug resistant HIV strains.

In a preferred embodiment, the instant invention provides an HIV protease inhibitor represented by a formula:

X-A-B-A'-X' wherein,

X is a moiety that contains two or more hydrogen bond acceptors capable of interacting with the backbone NH atoms of residues 29 and 30 of said protease;

A is a 2–6 atom linker that contains at least one hydrogen bond acceptor that interacts with the flap water, and one hydrogen bond donor that interacts with the backbone CO atom of residue 27 of said protease;

B contains 1–3 atoms that can form hydrogen bonds with either or both carboxylate side chain oxygens of Asp25 and Asp 125 of said protease;

A' is a 2–6 atom linker that contains at least one hydrogen bond acceptor that interacts with a flap water of said protease;

X' is a moiety that can form one or more hydrogen bonds with the backbone NH atoms of residues 129 and/or 130 of said protease.

In a particular embodiment the invention provides an HIV protease inhibitor represented by the formula I:

X-A-B-A'-X'        I wherein X is a moiety that contains two or more hydrogen bond acceptors capable of interacting with the backbone NH atoms of residues 29 and 30 of an HIV protease;

A is a 2–6 atom linker that contains at least one hydrogen bond acceptor that interacts with a flap water of said protease, and one hydrogen bond donor that interacts with the backbone CO atom of residue 27 of said proteease;

B contains 1–3 atoms that can form hydrogen bonds with either or both carboxylate side chain oxygens of Asp25 and Asp 125 of said protease;

A' is a 2–6 atom linker that contains at least one hydrogen bond acceptor that interacts with the flap water of said protease; and X' is a moiety that can form one or more hydrogen bonds with the backbone NH atoms of residues 129 and/or 130 of said protease; provided that the compound of Formula I is not any of the compounds described in *J. Med. Chem.* 39:3278–3290 (1996), in *Bioorg. Med. Chem. Lett.* 8:687–690 (1998), or *Bioorg. Med. Chem. Lett.* 8:979–982 (1998).

In another embodiment, the invention provides an HIV protease inhibitor represented by a formula:

X-A-B-A'-X' wherein:

X is independently a 5–7 membered non-aromatic monocyclic heterocycle, wherein said heterocycle is optionally fused with 1 or 2 3–7 membered non-aromatic monocyclic heterocycles, wherein said 5–7 membered non-aromatic monocyclic heterocycle is substituted by at least a group R4 on a carbon of said heterocycle adjacent to a heteroatom wherein R4 may optionally be part of the fused heterocycles; and wherein any of said heterocyclic ring systems has one or more heteroatoms selected from N, O, and S, wherein N is optionally substituted by R2 and S is optionally substituted by one or two oxygen atoms, and wherein any of said ring systems is optionally substituted 1 to 6 times by R5;

A is ZCONH, ZCOCONH, ZS(O)$_2$NH, ZP(O)(V)NH, CONH, COCONH, S(O)$_2$NH, P(O)(V)NH, wherein Z is O, NR2, C(R2)$_2$, and V is OR2, NR2;

B is,

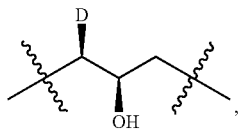

wherein D is selected from C1–C6 alkyl, C2–C4 alkenyl optionally substituted with one or more groups selected from C3–C7 cycloalkyl, C5–C7 cycloalkenyl, OR2, SR2, NHR2, OR3, SR3, NHR3, OR6, SR6, or NHR6;

A' is N(D')E', wherein D' is selected from C1–C15 alkyl, C2–C15 alkenyl or C2–C15 alkynyl, and E' is —CO— or —SO$_2$—;

X' is selected from the group consisting of R2, R3, and R6, provided that when X' is H, E' is not —SO$_2$—;

R2 is H or C1–C6 alkyl optionally substituted by R3, R5, or R6,

R3 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7;

R4 is N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, OH, OR8, OC(O)R8, OC(S)R8, OC(O)N(R8)$_2$, OC(S)N(R8)$_2$, OPO$_n$(R8)$_2$, R2OH, R2-halo, CN, COR8, CO$_2$R8, CON(R8)$_2$, C(O)N(R8)N(R8)$_2$, S(O)$_n$R8, SO$_2$N(R8)$_2$, halo, NO$_2$, or SR8;

R5 is OH, OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R2-halo, CN, COR8, CO$_2$R8, CON(R8)$_2$, C(O)N(R8)N(R8)$_2$, S(O)$_n$R8, SO$_2$N(R8)$_2$, halo, NO$_2$, SR8, oxo, =N—OH, =N—OR8, =N—N(R8)$_2$, =NR8, =NNR8C(O)N(R8)$_2$, =NNR8C(O)OR8, =NNR8S(O)$_n$N(R8)$_2$, or =NNR8S(O)$_n$(R8), =NNR8C(O)R8, or R5 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R5 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6;

R6 is aryl or heteroaryl, wherein said aryl or heteroaryl may be optionally substituted with one or more groups selected from the group consisting of aryl, heteroaryl, R2, R3, and R4;

R7 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, or CO$_2$R2; provided R2 is not H; CO$_2$R3, or CO$_2$R6

R8 is H or C1–C6 alkyl optionally substituted by R3, R5, or R6, or R8 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R8 is aryl or heteroaryl, wherein said aryl or heteroaryl may be optionally substituted with one or more groups selected from the group consisting of aryl, heteroaryl, R2, R3, R4, and R6;

Z is O, S;

each n is independently an integer between 1–2; its stereoisomeric forms; and its pharmacologically acceptable salts.

Preferably, X is

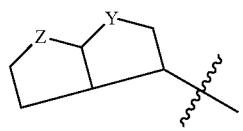

wherein
Y is O, NH, or S;
Z is O, NH, or S; and
wherein any ring carbon is optionally substituted by R2, R3, R5, R6.

Preferably X is

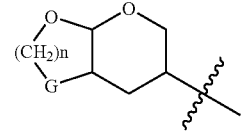

wherein
G is C, O, NR$_2$, or S;
n is an integer between 1–2; and
wherein any ring carbon is optionally substituted by R2, R3, R5, R6.

Preferably, X is

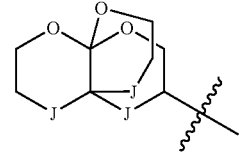

wherein
J is independently CH2, or O, or J is a bond; and
wherein any ring carbon is optionally substituted by R2, R3, R5, R6.

Preferably, X is

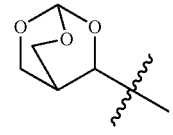

wherein any ring carbon is optionally substituted by R2, R3, R5, or R6.

Preferably, X is

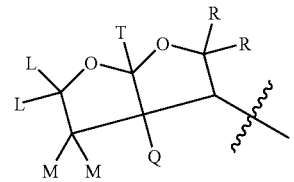

wherein
each L is independently H, lower alkyl, oxo, or L forms a carbocyclic or heterocyclic ring with M;
each M is independently H, OH, chloro, fluoro, or M forms a carbocyclic or heterocyclic ring with Q, provided that if one M is OH, the other M is not OH;
Q is H, OH, amino, lower alkyl, alkylamino, alkoxy, halo, or forms a 3–7-membered carbocyclic or heterocyclic ring together with T;
each R is independently H, OH, lower alkyl, halo, or spirocylopropyl, provided that if one R is OH, the other R is not OH;
T is H or F, or T forms a carbocyclic or heterocyclic ring together with C;

In another preferred embodiment, the invention also provides an HIV protease inhibitor represented by a formula:

X-A-B-A'-X' wherein:

X is a 5–7 membered non-aromatic monocyclic heterocycle, wherein said heterocycle is fused with at least one 3–7 membered non-aromatic monocyclic heterocycle to form a polycyclic system, preferably bicyclic, wherein at least one carbon atom is substituted by two heteroatoms; and wherein any of said heterocyclic ring systems contains one or more heteroatoms selected from O, N, S; wherein any nitrogen forming part of the heterocycles may optionally be substituted by R2, R3, R6, R7 or O; wherein any sulfur may be optionally be substituted by one or two oxygen atoms; and any of said ring systems optionally contains 1 to 6 substituents selected from the group consisting of R2, R3, R5, and R6;

A is ZCZNH; wherein Z is independently NR2, O, or S; B is,

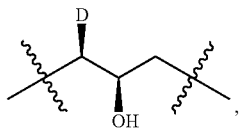

wherein D is alkyl, alkenyl, alkynyl, aryl, cycloalkyl, or aralkyl optionally substituted by alkyl, halo, nitro, cyano, CF3, O-alkyl or S-alkyl;

A' is N(D')E', wherein D' is alkyl, alkenyl, alkynyl aryl, cycloalkyl, or aralkyl optionally substituted by alkyl, halo, CF$_3$, and E' is SO$_2$;

X' is selected from the group consisting of aryl and heteroaryl, which are substituted with one or more of the following groups:

OR3, OR6, OR7, OR2 provided R2 is not H or unsubstituted alkyl;

alkyl substituted by R3, R5, R6 provided R5 is not halo;

C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7;

aryl or heteroaryl, wherein said aryl or heteroaryl may be optionally substituted with one or more groups selected from the group consisting of aryl, heteroaryl, R2, R3, R4, and R6;

C3–C7 cycloalkyl substituted by R2, R3, R5, R6; provided R2 is not H;

CO$_2$H, R7 provided Z is N, O, S and provided R2 is not H or unsubstituted alkyl;

NR3R3, NR6R6, NR7R7, NR3R6, NR6R7, NR3R7, NR2R3, NR2R6, NR2R7, NR2R2 provided R2 is not H or unsubstituted alkyl;

SO$_n$N(R2)$_2$, SO$_n$N(R3)$_2$, SO$_n$N(R6)$_2$, SO$_n$N(R7)$_2$, SO$_n$NR2R3, SO$_n$NR2R6, SO$_n$NR2R7, SO$_n$NR3R6, SO$_n$NR3R7, SO$_n$NR6R7, wherein n=1 or 2;

S(O)$_n$R2, S(O)$_n$R3, S(O)$_n$R6, provided R2 is not H or methyl; and n is 0, 1 or 2;

R2 is H or C1–C6 alkyl optionally substituted by R3, R5, or R6,

R3 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7;

R4 is N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, OH, OR8, OC(O)R8, OC(S)R8, OC(O)N (R8)$_2$, OC(S)N(R8)$_2$, OPO$_n$(R8)$_2$, R2OH, R2-halo, CN, COR8, CO$_2$R8, CON(R8)$_2$, C(O)N(R8)N(R8)$_2$, S(O)$_n$R8, SO$_2$N(R8)$_2$, halo, NO$_2$, or SR8;

R5 is OH, OR8, N(R8)$_2$, NHOH, N(R8)COR8, NR8S(O) nR8, NR8C[=N(R8)]N(R8)$_2$, N(R8)N(R8)C(O)R8, NR8POnNR8R8, NR8POnOR8, R2OH, R2-halo, CN, COR8, CO$_2$R8, CON(R8)$_2$, C(O)N(R8)N(R8)$_2$, S(O)nR8, SO$_2$N(R8)$_2$, halo, NO$_2$, SR8, oxo, =N—OH, =N—OR8, =N—N(R8)$_2$, =NR8, =NNR8C(O)N(R8)$_2$, =NNR8C (O)OR8, =NNR8S(O)nN(R8)$_2$, =NNR8S(O)n(8), or =NNR8S(O)n(R8), or R5 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R5 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6;

R6 is aryl or heteroaryl, wherein said aryl or heteroaryl may be optionally substituted with one or more groups selected from the group consisting of aryl, heteroaryl, R2, R3, and R4;

R7 is C(O)R2, C(O)R3, C(O)R6, C(S)R2, C(S)R3, C(S) R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6

R8 is H and C1–C6 alkyl optionally substituted by R3, R5, or R6, or R8 is C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)NHR2, S(O)nN(R2)(R2), CN, SR2, SOnR2, COR2, CO2R2 or NR2C(O)R2, R5, and R7;

or R8 is aryl or heteroaryl, wherein said aryl or heteroaryl may be optionally substituted with one or more groups selected from the group consisting of aryl, heteroaryl, R2, R3, R4, and R6;

Z is O, S;

each n is independently an integer between 1–2;

its stereoisomeric forms; and its pharmacologically acceptable salts.

In another preferred embodiment, the invention also provides an HIV protease inhibitor represented by a formula:

X-A-B-A'-X' wherein:

X is tetrahydrofurodihydrofuranyl, tetrahydrofurotetrahydrofuranyl, tetrahydropyranotetrahydrofuranyl or tetrahydropyranodihydrofuranyl;

A is OCONH;

B is,

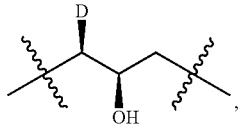

wherein D is alkyl, alkenyl, alkynyl, aryl, cycloalkyl, or aralkyl optionally substituted by alky, halo, nitro, cyano, CF$_3$, O-alkyl or S-alkyl;

A' is N(D')E', wherein D' is alkyl, alkenyl, alkynyl aryl, cycloalkyl, or aralkyl optionally substituted by alkyl, halo, or CF$_3$, and E' is —SO$_2$—;

X' is selected from the group consisting of aryl and heteroaryl, which are substituted with one or more groups selected from the group consisting of:

OR3, OR6, OR7, or OR2 provided R2 is not H or unsubstituted alkyl;

alkyl substituted by R3, R5, or R6 provided R5 is not halo;

C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)NHR2, S(O)nN(R2)(R2), CN, SR2, SOnR2, COR2, CO$_2$R2 or NR2C(O)R2, R5, and R7;

aryl or heteroaryl, wherein said aryl or heteroaryl may be optionally substituted with one or more groups selected from the group consisting of aryl, heteroaryl, R2, R3, R4, and R6;

C3–C7 cycloalkyl substituted by R2, R3, R5, or R6; provided R2 is not H;

CO$_2$H, or R7 where Z=N, O, S and provided R2 is not H or unsubstituted alkyl

NR3R3, NR6R6, NR7R7, NR3R6, NR6R7, NR3R7, NR2R3, NR2R6, NR2R7, NR2R2 provided R2 is not H or unsubstituted alkyl;

SOnN(R2)2, SOnN(R3)2, SOnN(R6)$_2$, SOnN(R7)$_2$, SOnNR2R3, SOnNR2R6, SOnNR2R7, SOnNR3R6, SOnNR3R7, SOnNR6R7, n=1 or 2;

S(O)nR2, S(O)nR3, S(O)nR6, provided R2 is not H or methyl; n is 0, 1 or 2;

R2 is H or C1–C6 alkyl optionally substituted by R3, R5, or R6,

R3 is C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)N(R2)$_2$, S(O)nN(R2)(R2), CN, SR2, SOnR2, COR2, CO$_2$R2 or NR2C(O)R2, R5, and R7;

R4 is N(R8)$_2$, NHOH, N(R8)COR8, NR8S(O)nR8, NR8C[=N(R8)]N(R8)$_2$, N(R8)N(R8)C(O)R8, NR8POnNR8R8, NR8POnOR8, OH, OR8, OC(O)R8, OC(S)R8, OC(O)N(R8)$_2$, OC(S)N(R8)$_2$, OPOn(R8)$_2$R2OH, R2-halo, CN, COR8, CO$_2$R8, CON(R8)$_2$, C(O)N(R8)N(R8)$_2$, S(O)nR8, SO$_2$N(R8)$_2$, halo, NO$_2$, or SR8;

R5 is OH, OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R2-halo, CN, COR8, CO$_2$R8, CON(R8)$_2$, C(O)N(R8)N(R8)$_2$, S(O)$_n$R8, SO$_2$N(R8)$_2$, halo, NO$_2$, SR8, oxo, =N—OH, =N—OR8, =N—N(R8)$_2$, =NR8, =NNR8C(O)N(R8)$_2$, =NNR8C(O)OR8, =NNR8S(O)$_n$N(R8)$_2$, or =NNR8S(O)$_n$(R8), =NNR8C(O)R8, or R5 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R5 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6;

R6 is aryl or heteroaryl, wherein said aryl or heteroaryl may be optionally substituted with one or more groups selected from the group consisting of aryl, heteroaryl, R2, R3, and R4;

R7 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6;

R8 is H or C1–C6 alkyl optionally substituted by R3, R5, or R6, or R8 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R8 is aryl or heteroaryl, wherein said aryl or heteroaryl may be optionally substituted with one or more groups selected from the group consisting of aryl, heteroaryl, R2, R3, R4, and R6;

Z is O, S;

each n is independently an integer between 1–2; its stereoisomeric forms; and its pharmacologically acceptable salts.

In another preferred embodiment, the invention also provides anHIV protease inhibitor represented by a formula:

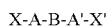

wherein:
X is tetrahydrofurotetrahydrofuranyl;
A is OCONH;
B is,

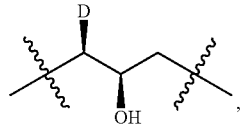

wherein D is benzyl

A' is N(D')E', wherein D' is isobutyl and E' is —SO$_2$—;

X' is selected from the group consisting of aryl and heteroaryl, which are substituted with one or more groups selected from the group consisting of:

OR3, OR6, OR7, OR2 provided R2 is not H or unsubstituted alkyl;

alkyl substituted by R3, R5, R6 provided R5 is not halo;

C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)NHR2, S(O)nN(R2)(R2), CN, SR2, SOnR2, COR2, CO$_2$R2 NR2C(O)R2, R5, and R7;

aryl or heteroaryl, wherein said aryl or heteroaryl may be optionally substituted with one or more groups selected from the group consisting of aryl, heteroaryl, R2, R3, R4, and R6;

C3–C7 cycloalkyl substituted by R2, R3, R5, R6; provided R2 is not H;

CO$_2$H, R7 where Z=N, O, or S provided R2 is not H or unsubstituted alkyl

NR3R3, NR6R6, NR7R7, NR3R6, NR6R7, NR3R7, NR2R3, NR2R6, NR2R7, or NR2R2 provided R2 is not H or unsubstituted alkyl;

SOnN(R2)$_2$, SOnN(R3)$_2$, SOnN(R6)$_2$ SOnN(R7)$_2$, SOnNR2R3, SOnNR2R6, SOnNR2R7, SOnNR3R6, SOnNR3R7, or SOnNR6R7, wherein n=1 or 2;

S(O)nR2, S(O)nR3, S(O)nR6, provided R2 is not H or methyl; wherein n is 0, 1 or 2;

R2 is H and C1–C6 alkyl optionally substituted by R3, R5, or R6,

R3 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)N(R2)$_2$, S(O)$_n$N(R2)$_2$, CN, SR2, SOnR2, COR2, CO$_2$R2 or NR2C(O)R2, R5, and R7;

R4 is N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, OH, OR8, OC(O)R8, OC(S)R8, OC(O)N(R8)$_2$, OC(S)N(R8)$_2$, OPO$_n$(R8)$_2$, R2OH, R2-halo, CN, COR8, CO$_2$R8, CON(R8)$_2$, C(O)N(R8)N(R8)$_2$, S(O)$_n$R8, SO$_2$N(R8)$_2$, halo, NO$_2$, or SR8;

R5 is OH, OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R2-halo, CN, COR8, CO$_2$R8, CON(R8)$_2$, C(O)N(R8)N(R8)$_2$, S(O)$_n$R8, SO$_2$N(R8)$_2$, halo, NO$_2$, SR8, oxo, =N—OH, =N—OR8, =N—N(R8)$_2$, =NR8, =NNR8C(O)N(R8)$_2$, =NNR8C(O)OR8, =NNR8S(O)$_n$N(R8)$_2$, or =NNR8S(O)$_n$(R8), =NNR8C(O)R8, or R5 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R5 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6;

R6 is aryl or heteroaryl, wherein said aryl or heteroaryl may be optionally substituted with one or more groups selected from the group consisting of aryl, heteroaryl, R2, R3, and R4;

R7 is C(O)R2, C(O)R3, C(O)R6, C(S)R2, C(S)R3, C(S)R6, C(Z)N(R2)$_2$, C(Z)N(R3)$_2$, C(Z)N(R6)$_2$, C(Z)NR2R3, C(Z)NR2R6, C(Z)NR3R6, CO$_2$R2; provided R2 is not H; CO$_2$R3, or CO$_2$R6

R8 is H or C1–C6 alkyl optionally substituted by R3, R5, or R6, or R8 is C2–C6 alkenyl, C2–C6 alkynyl, C3–C8 cycloalkyl, C5–C8 cycloalkenyl, or heterocyclo, which groups may be optionally substituted with one or more substituents selected from the group consisting of —OR2, C(O)NR2, S(O)$_n$N(R2)$_2$, CN, SR2, SO$_n$R2, COR2, CO$_2$R2 or NR2C(O)R2, R5, and R7, or R8 is aryl or heteroaryl, wherein said aryl or heteroaryl may be optionally substituted with one or more groups selected from the group consisting of aryl, heteroaryl, R2, R3, R4, and R6;

Z is O, S;

each n is independently an integer between 1–2; its stereoisomeric forms; and its pharmacologically acceptable salts.

Preferably, X is

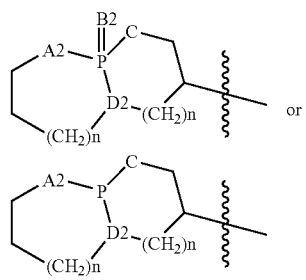

wherein A2, B2, and C are each independently O, NR2, or S;

D2 is CH or N; and wherein any ring carbon is optionally substituted by R2, R3, R5, or R6.

Preferably, X is

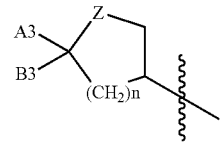

wherein

A3 is H, F or alkoxy;

B3 is F, alkoxy, lower alkyl, or A and B can form a 3–7 membered heterocyclic ring;

Z is O, NR2, or S;

n is an integer between 1–3; and wherein any ring carbon is optionally substituted by R2, R3, R5, R6.

With regard to X, X may also be a 5–7 membered non-aromatic monocyclic heterocycle, wherein said heterocycle is optionally fused or bridged with one or more 3–7 membered non-aromatic monocyclic heterocycle to form a polycyclic system, wherein any of said heterocyclic ring systems contains one or more heteroatoms selected from O, N, S, or P; wherein any nitrogen forming part of the heterocycles may optionally be substituted by R2, R3, R6, R7 or O; wherein any sulfur may be optionally be substituted by one or two oxygen atoms; wherein any P may be optionally be substituted by one or more of O NR2, or S, and any of said ring systems optionally contains 1 to 6 substituents selected from the group consisting of R2, R3, R5, and R6.

X may also be

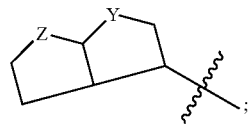

wherein, Y is O, NH, or S; Z is O, NH, or S; and wherein any ring carbon is optionally substituted by R2, R3, R5, or R6.

X may also be

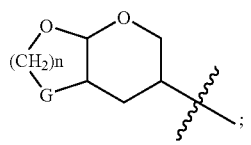

wherein G is C, O, NR2, or S; n is an integer between 1–2; and wherein any ring carbon is optionally substituted by R2, R3, R5, or R6.

X may also be

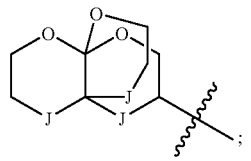

wherein J is independently CH$_2$, or O, and wherein any ring carbon is optionally substituted by R2, R3, R5, or R6.

X may also be

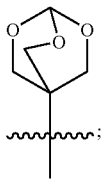

wherein any ring carbon is optionally substituted by R2, R3, R5, or R6.

X may also be

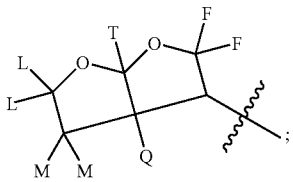

wherein each L is independently H, lower alkyl, oxo, or L forms a carbocyclic or heterocyclic ring with M; each M is independently H, OH, chloro, fluoro, or M forms a carbocyclic or heterocyclic ring with Q, provided that if one M is OH, the other M is not OH; Q is H, OH, amino, lower alkyl, alkylamino, alkoxy, halo, or forms a 3–7-membered carbocyclic or heterocyclic ring together with T; each F is independently H, OH, lower alkyl, halo, or spirocylopropyl, provided that if one R is OH, the other R is not OH; T is H or F, or T forms a carbocyclic or heterocyclic ring together with F.

X may also be

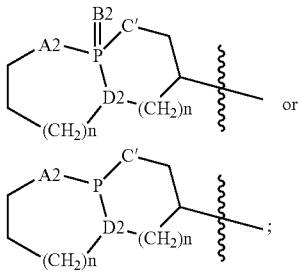

wherein A2, B2, and C' are each independently O, NR2, or S; D2 is CH or N; and n is an integer between 1 and 2.

X may also be

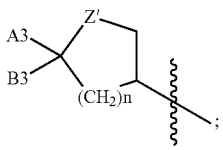

wherein A3 is H, F or alkoxy; B3 is F, alkoxy, lower alkyl, or A3 and B3 can form a 3–7 membered heterocyclic ring; Z' is O, NR2, or S; and n is an integer between 1–3.

X is preferably tetrahydrofurodihydrofuranyl, tetrahydrofuro-tetrahydrofuranyl, tetrahydropyrano-tetrahydrofuranyl or tetrahydropyranodihydrofuranyl. More preferably, X is tetrahydrofurotetrahydrofuranyl.

With regard to A, A may be ZCZNH, ZCOCONH, ZS(O)$_2$NH, ZP(O)(V)NH, CONH, COCONH, S(O)$_2$NH, P(O)(V)NH, wherein Z is NR2, O, S, or C(R2)$_2$, and V is OR2 or NR2. A is preferably OCONH.

With regard to B, B may be,

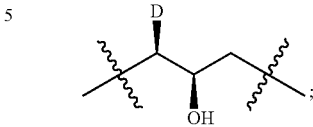

wherein D is selected from alkyl, alkenyl, alkynyl, aryl, cycloalkyl, or aralkyl optionally substituted with one or more groups selected from alkyl, halo, nitro, cyano, CF$_3$, C3–C7 cycloalkyl, C5–C7 cycloalkenyl, R6, OR2, SR2, NHR2, OR3, SR3, NHR3, OR6, SR6, or NHR6.

With regard to A', A' may be N(D')E', wherein D' is selected from alkyl, alkenyl, alkynyl, aryl, cycloalkyl, or aralkyl optionally substituted by alkyl, halo, nitro, cyano, CF$_3$, O-alkyl, or S-alkyl, and E' is —CO— or —SO$_2$—. Preferably, D' is alkyl, alkenyl, alkynyl aryl, cycloalkyl, or aralkyl optionally substituted by alkyl, halo, or CF$_3$, and E' is —SO$_2$—. More preferably, D' is isobutyl and E' is —SO$_2$—.

With regard to X', X' is selected from the group consisting of aryl and heteroaryl, which are substituted with one or more of the following groups: OR3, OR6, OR7, OR2 provided R2 is not H or unsubstituted alkyl; alkyl substituted by R3, R5, R6 provided R5 is not halo; C2–C6 alkenyl, C2–C6 alkynyl, C3–C8 cycloalkyl, C5–C8 cycloalkenyl, and heterocyclo, which groups may be optionally substituted with one or more substituents selected from R5; aryl or heteroaryl, wherein said aryl or heteroaryl may be optionally substituted with one or more groups selected from the group consisting of aryl, heteroaryl, R2, R3, R4, and R6; C3–C7 cycloalkyl substituted by R2, R3, R5, R6; provided R2 is not H; CO$_2$H or R7; provided R8 is not H or unsubstituted alkyl; NR8R8, NR7R8, NR7R7; provided R8 is not H or unsubstituted alkyl; SO$_n$N(R8)$_2$, SO$_n$NR7R8, SR8, S(O)$_n$R8, provided R8 is not H or methyl; and n is 1 or 2.

X' may also be

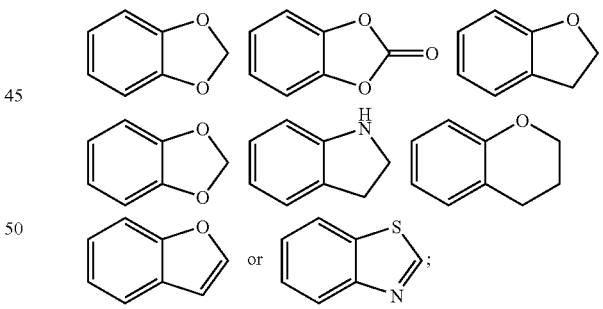

wherein said groups are substituted with one or more of the following groups: OR3, OR6, OR7, OR2 provided R2 is not H or unsubstituted alkyl; alkyl substituted by R3, R5, R6 provided R5 is not halo; C2–C6 alkenyl, C2–C6 alkynyl, C3–C8 cycloalkyl, C5–C8 cycloalkenyl, and heterocyclo, which groups may be optionally substituted with one or more substituents selected from R5; aryl or heteroaryl, wherein said aryl or heteroaryl may be optionally substituted with one or more groups selected from the group consisting of aryl, heteroaryl, R2, R3, R4, and R6; C3–C7 cycloalkyl substituted by R2, R3, R5, R6; provided R2 is not H; CO$_2$H or R7; provided R8 is not H or unsubstituted alkyl; NR8R8, NR7R8, NR7R7; provided R8 is not H or unsubstituted alkyl; $SO_n(R8)_2$, $SO_nNR7R8$, SR8, $S(O)_nR8$, provided R8 is not H or methyl; and n is 1 or 2.

X' may also be

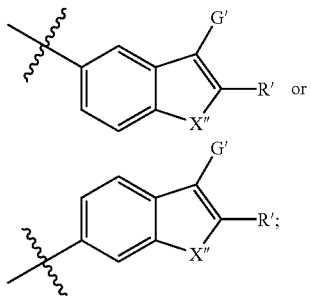

wherein G' and R' cannot both be H; G' and R' are each independently: H or alkyl substituted by R3, R5, R6 provided R5 is not halo; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, $C(O)N(R2)_2$, $S(O)_nN(R2)_2$, CN, SR, $SO_nR2$, COR2, $CO_2R2$ or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl substituted by R2, R3, R5, R6; provided R2 is not H; $CO_2H$ or R7 provided R2 is not H or unsubstituted alkyl; $SO_nN(R8)_2$, $SO_nNR7R8$, SR8, $S(O)_nR8$, provided R8 is not H or methyl; and n is 1 or 2; and X" is selected from O or NR"; wherein R" is H or alkyl optionally substituted by R3, R5, R6; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, $C(O)N(R2)_2$, $S(O)_nN(R2)_2$, CN, SR2, $SO_nR2$, COR2, $CO_2R2$ or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl optionally substituted by R2, R3, R5, R6; R7; NR3R3, NR6R6, NR7R7, NR3R6, NR6R7, NR3R7, NR2R3, NR2R6, NR2R7, NR2R2; $SO_nN(R2)_2$, $SO_nN(R3)_2$, $SO_nN(R6)_2$, $SO_nN(R7)_2$, $SO_nNR2R3$, $SO_nNR2R6$, $SO_nNR2R7$, $SO_nNR3R6$, $SO_nNR3R7$, $SO_nNR6R7$; $S(O)_mR2$, $S(O)_mR3$, $S(O)_mR6$, provided R2 is not H; and m is 0, 1 or 2.

X' may also be

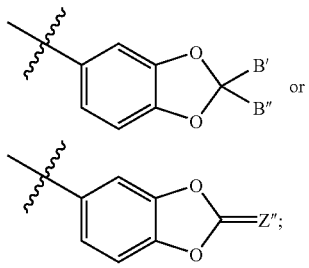

wherein B' and B" cannot both be H or methyl; B' and B" are independently: H or alkyl optionally substituted by R3, R5, R6; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, $C(O)N(R2)_2$, $S(O)_nN(R2)_2$, CN, SR2, $SO_nR2$, COR2, $CO_2R2$ or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl optionally substituted by R2, R3, R5, R6; $CO_2H$ or R7; $SO_nN(R2)_2$, $SO_nN(R3)_2$, $SO_nN(R6)_2$, $SO_nN(R7)_2$, $SO_nNR2R3$, $SO_nNR2R6$, $SO_nNR2R7$, $SO_nNR3R6$, $SO_nNR3R7$, $SO_nNR6R7$; $S(O)_mR2$, $S(O)_mR3$, $S(O)_mR6$; $SO_nN(R8)_2$, $SO_nNR7R8$, SR8, $S(O)_nR8$, provided R8 is not H or methyl; and n is 1 or 2; and m is 0, 1 or 2; Z" is O, NR9; R9 is alkyl optionally substituted by R3, R5, R6; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, $C(O)N(R2)_2$, $S(O)_nN(R2)_2$, CN, SR2, $SO_nR2$, COR2, $CO_2R2$ or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl optionally substituted by R2, R3, R5, R6; $CO_2H$ or R7; NR3R3, NR6R6, NR7R7, NR3R6, NR6R7, NR3R7, NR2R3, NR2R6, NR2R7, NR2R2; $SO_nN(R2)_2$, $SO_nN(R3)_2$, $SO_nN(R6)_2$, $SO_nN(R7)_2$, $SO_nNR2R3$, $SO_nNR2R6$, $SO_nNR2R7$, $SO_nNR3R6$, $SO_nNR3R7$, $SO_nNR6R7$; $S(O)_mR2$, $S(O)_mR3$, $S(O)_mR6$, provided R2 is not H; and m is 0, 1 or 2.

X' may also be

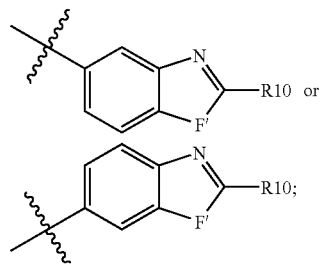

wherein R10 is alkyl substituted by R3, R5, R6 provided R5 is not halo; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, $C(O)N(R2)_2$, $S(O)_nN(R2)_2$, CN, SR2, $SO_nR2$, COR2, $CO_2R2$ or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl substituted by R2, R3, R5, R6; provided R2 is not H; R7 provided Z is N, O, S and provided R2 is not H or unsubstituted alkyl; and F' is O or S.

X' may also be

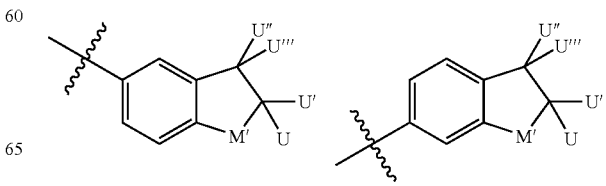

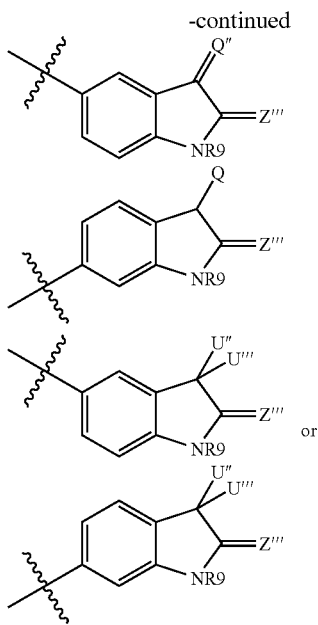

Wherein U and U' are each independently H or alkyl substituted by R3, R5, R6; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl substituted by R2, R3, R5, R6; CO$_2$H, R7; SO$_n$N(R8)$_2$, SO$_n$NR7R8, SR8, S(O)$_n$R8, provided R8 is not H or methyl; and n is 1 or 2; SO$_n$N(R2)$_2$, SOnN(R3)$_2$, SO$_n$N(R6)$_2$, SO$_n$N(R7)$_2$, SO$_n$NR2R3, SO$_n$NR2R6, SO$_n$NR2R7, SO$_n$NR3R6, SO$_n$NR3R7, SO$_n$NR6R7, wherein n=1 or 2; S(O)$_m$R2, S(O)$_m$R3, S(O)$_m$R6, provided R2 is not H; and n is 0, 1 or 2.

U''' and U'''' are each independently H, OR3, OR6, OR7, OR2; alkyl substituted by R3, R5, R6; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl substituted by R2, R3, R5, R6; CO$_2$H or R7; NR3R3, NR6R6, NR7R7, NR3R6, NR6R7, NR3R7, NR2R3, NR2R6, NR2R7, NR2R2; SO$_n$N(R8)$_2$, SO$_n$NR7R8, SR8, S(O)$_n$R8, provided R8 is not H or methyl; and n is 1 or 2; SO$_n$N(R2)$_2$, SO$_n$N(R3)$_2$, SO$_n$N(R6)$_2$, SO$_n$N(R7)$_2$, SO$_n$NR2R3, SO$_n$NR2R6, SO$_n$NR2R7, SO$_n$R3R6, SO$_n$NR3R7, SO$_n$NR6R7; S(O)$_m$R2, S(O)$_m$R3, S(O)$_m$R6, provided R2 is not H; and m is 0, 1 or 2; U and U' cannot both be H unless one of U'' and U''' is not H; U'' and U''' cannot both be H unless one of U and U' is not H; M' is O, NR9, or NH, except where R9 is CO$_2$H; Z''' is O or NR9; Q' is O, NR9, or CU''U'''.

R9 is alkyl optionally substituted by R3, R5, R6; C2–C6 alkenyl, C2–C6 alkynyl, C3–C8 cycloalkyl, C5–C8 cycloalkenyl, and heterocyclo, which groups may be optionally substituted with one or more substituents selected from the group consisting of —OR2, C(O)N(R2)$_2$, S(O)$_n$N(R)$_2$, CN, SR2, SO$_n$R2, COR2, CO$_2$R2 or NR2C(O)R2, R5, and R7; aryl or heteroaryl, wherein said aryl or heteroaryl may be optionally substituted with one or more groups selected from the group consisting of aryl, heteroaryl, R2, R3, R4, and R6; C3–C7 cycloalkyl optionally substituted by R2, R3, R5, R6; CO$_2$H or R7; NR3R3, NR6R6, NR7R7, NR3R6, NR6R7, NR3R7, NR2R3, NR2R6, NR2R7, NR2R2; SO$_n$N(R8)$_2$, SO$_n$NR7R8, SR8, S(O)$_n$R8, provided R8 is not H or methyl; and n is 1 or 2; SO$_n$N(R2)$_2$, SO$_n$N(R3)$_2$, SO$_n$N(R6)$_2$, SO$_n$N(R7)$_2$, SO$_n$NR2R3, SO$_n$NR2R6, SO$_n$NR2R7, SO$_n$NR3R6, SO$_n$NR3R7, SO$_n$NR6R7; S(O)$_m$R2, S(O)$_m$R3, S(O)$_m$R6, provided R2 is not H; and m is 0, 1 or 2.

Preferably, R is H or alkyl, aryl, alkenyl, alkynyl, cycloalkyl, cycloalkenyl, heterocyclo, heteroaryl; optionally substituted by halo, hydroxy, alkoxy, aryloxy, cycloalkoxy, heteroaryloxy, cyano, nitro, alkylthio, arylthio, cycloalkylthio, amino, or mono- or dialkylamino, mono- or diarylamino, mono- or di-cycloalkylamino, mono- or di-heteroarylamino, alkanoyl, cycloalkanoyl, aroyl, heteroaroyl, carboxamido, mono- or dialkylcarboxamido, mono- or diarylcarboxamido, sulfonamido, mono- or dialkylsulfonamido, mono- or diarylsulfonamido, alkylsulfinyl, alkylsulfonyl, arylsulfinyl, arylsulfonyl, cycloalkylsulfinyl, cycloalkylsulfonyl, heteroarylsulfinyl, heteroarylsulfonyl.

Prererably, R2 is H or C1–C6 alkyl; optionally substituted by C2–C6 alkenyl, C2–C6 alkynyl, C3–C8 cycloalkyl, C5–C8 cycloalkenyl, heterocyclo; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, —NNRC(O)N(R)$_2$, =NNRCON$_n$R, =NNRS(O)$_n$N(R)$_2$, or =NNRS(O)$_n$(R); or R2 is C1–C6 alkyl; substituted by aryl or heteroaryl; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR; or R2 is C1–C6 alkyl; optionally substituted by halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, —NR, =NNRC(O)N(R)$_2$, =NNRCOnR, =NNRS(O)nN(R)$_2$, or =NNRS(O)n(R).

Preferably, R3 is C2–C6 alkenyl, C2–C6 alkynyl, C3–C8 cycloalkyl, C5–C8 cycloalkenyl, or heterocyclo; which groups may be optionally substituted with one or more substituents selected from the group consisting of halo, OR2, R2—OH, R2-halo, NO$_2$, CN, CO$_n$R2, C(O)N(R2)$_2$, C(O)N(R2)N(R2)$_2$, C(S)R2, C(S)N(R2)$_2$, S(O)nN(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, NR2PO$_n$N(R2)$_2$, NR2PO$_n$OR2, oxo, =N—OR2, =N—N(R2)$_2$, =NR2, =NNRC(O)N(R2)$_2$, =NNR2C(O)$_n$R2, =NNR2S(O)$_n$N(R2)$_2$, or =NNR2S(O)$_n$(R2).

Preferably, R4 is halo, OR8, R—OH, R3—OH, R2-halo, R3-halo, NO$_2$, CN, CO$_n$R8, CO$_n$R8, CON(R8)$_2$, C(O)N(R8)N(R8)$_2$, C(S)R8, C(S)N(R8)$_2$, SOnN(R8)$_2$, SR8, SO$_n$R8, N(R8)$_2$, N(R8)CO$_n$R8, NR8S(O)$_n$R8, NR8C[=N(R8)]N(R8)$_2$, N(R8)N(R8)CO$_n$R8, NR8PO$_n$N(R8)$_2$, NR8PO$_n$OR8, OC(O)R2, OC(S)R8, OC(O)N(R8)$_2$, OC(S)N(R8)$_2$, OPO$_n$(R8)$_2$.

Preferably, R5 is OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R3—OH, R2-halo, R3-halo, CN, CO$_n$R8; provided that when n=2, R8 is not H; CON(R8)$_2$, C(O)N(R8)N(R8)$_2$, C(S)$_n$RS, C(S)N(R8)$_2$, S(O)nR8, SO$_n$N(R8)$_2$, halo, NO$_2$, SR8, oxo, =N—OH, =N—OR8, =N—N(R8)$_2$, =NR8, =NNR8C(O)N(R8)$_2$, =NNR8C(O)$_n$R8, =NNR8S(O)$_n$N(R8)$_2$, or =NNR8S(O)$_n$(R8), or R3.

Preferably, R6 is aryl or heteroaryl, wherein said aryl or heteroaryl may be optionally substituted with one or more groups selected from aryl, heteroaryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, NR2PO$_n$N(R2)$_2$, NR2PO$_n$OR2, OC(O)R2, OC(S)R2, OC(O)N(R2)$_2$, OC(S)N(R2)$_2$, OPO$_n$(R2)$_2$.

Preferably, R7 is C(O)$_n$R8; provided that when n=2; R8 is not H; C(S)R8, C(O)N(R8)$_2$, C(S)N(R8)$_2$, S(O)$_n$R8, S(O)nN(R8)$_2$.

Preferably, R8 is R2, R3, or R6; and Z is N, O, or S.

FIG. 7 describes a set of three-dimensionally-conserved substructures of an HIV protease substrate binding site and the substructure of atoms of an inhibitor interacting with the conserved substructure of the protease. The substructures are defined by the set of atomic coordinates, referred to an orthogonal system of coordinates shown below. The skilled artisan will recognize that any set of coordinates derived by applying arbitrary rotations and translations to the set of atomic coordinates in this table will be equivalent to the coordinates shown. The values of the coordinates (x,y,z) of the atoms defining the substructure are affected by a standard error σ. Therefore (x,y,z) values for each atom are those defined in the intervals (x−σ, x+σ) for coordinate x, (y−σ, y+σ) for coordinate y, and (z−σ, z+σ) for coordinate z.

Accordingly, the invention provides an HIV protease inhibitor having the formula I:

wherein X is a moiety comprising first and second hydrogen bond acceptor atoms H$_{A1}$:X and H$_{A2}$:X, wherein H$_{A1}$:X forms a hydrogen bond with N29 of HIV protease and H$_{A2}$:X forms a hydrogen bond with N30 of HIV protease at the relative positions designated in Table 8;

wherein A is an optionally substituted linker moiety comprising a linear chain of 2–6 atoms, wherein A comprises a hydrogen bond acceptor atom H$_A$:A, and a hydrogen bond donor atom H$_D$:A, and wherein H$_A$:A forms a hydrogen bond with solvated water301 of said protease at a relative position designated by O301, and HD:A forms a hydrogen bond with the backbone CO atom of residue 27 of said protease at a relative position designated by O27;

wherein B comprises a hydrogen bond donor or acceptor atom H$_{D/A}$:B, wherein H$_{D/A}$:B forms a hydrogen bond with either or both carboxylate side chain oxygens of Asp25 and Asp 125 of said protease at relative positions designated by OD1 25, OD2 25, OD1 125, and OD2 125;

wherein A' is an optionally substituted linker moiety comprising a linear chain of 2–6 atoms, comprising a hydrogen bond acceptor atom H$_A$:A', wherein H$_A$:A' forms a hydrogen bond with solvated water301 of said protease at a relative position designated by O301; and wherein X' is a moiety comprising a hydrogen bond acceptor atom H$_A$:X', wherein H$_A$:X' forms a hydrogen bond with backbone NH atoms of residues 129 and/or 130 of said protease at relative positions designated by N129 and/or N130.

The compound of Formula I specifically can not be any of the compounds described in *J. Med. Chem.* 39:3278–3290 (1996), in *Bioorg. Med. Chem. Lett.* 8:687–690 (1998), or *Bioorg. Med. Chem. Lett.* 8:979–982 (1998), which compounds are specifically disclaimed herein. The HIV inhibitors described in the following documents also are specifically disclaimed: EP00/9917, WO00/76961, WO99/65870, WO02/083657, WO02/081478, WO02/092595, WO99/67417, and U.S. Pat. Nos. 5,990,155 and 6,319,946, the contents of which are incorporated herein by reference.

In another preferred embodiment, the invention also provides compounds of the instant invention bound in a complex with wild type or drug resistant mutant forms of HIV-1 protease.

In another preferred embodiment, the invention also provides a composition comprising an inhibitor according to to the instant invention and a pharmaceutically acceptable additive, excipient, or diluent.

In another preferred embodiment, the invention also provides an pharmaceutical composition comprising an inhibitor according to the instant invention and another antiretroviral agent.

In another preferred embodiment, the invention also provides a composition comprising an inhibitor according to thew instant invention and a second HIV inhibitor;

In another preferred embodiment, the invention also provides an inhibitor according to the instant invention and an additional HIV protease inhibitor.

In another preferred embodiment, the invention also provides an inhibitor according to the instant invention and an HIV reverse transcriptase inhibitor.

In another preferred embodiment, the invention also provides a method of treating a patient suffering from HIV infection, comprising administering to said patient a composition according to the instant invention. Preferably, the patient is suffering from a multi-drug resistant HIV infection.

The term "alkyl", alone or in combination with any other term, refers to a straight-chain or branch-chain saturated aliphatic hydrocarbon radical containing the specified number of carbon atoms, or where no number is specified, preferably from 1 to about 15 and more preferably from 1 to about 10 carbon atoms. Examples of alkyl radicals include, but are not limited to, methyl, ethyl, n-propyl, isopropyl, n-butyl, isobutyl, sec-butyl, tert-butyl, pentyl, isoamyl, n-hexyl and the like.

The term "alkenyl", alone or in combination with any other term, refers to a straight-chain or branched-chain mono- or poly-unsaturated aliphatic hydrocarbon radical containing the specified number of carbon atoms, or where no number is specified, preferably from 2–10 carbon atoms and more preferably, from 2–6 carbon atoms. Examples of alkenyl radicals include, but are not limited to, ethenyl, E- and Z-propenyl, isopropenyl, E- and Z-butenyl, E- and Z-isobutenyl, E- and Z-pentenyl, E- and Z-hexenyl, E,E-, E,Z-, Z,E- and Z,Z-hexadienyl and the like.

The term "alkynyl," alone or in combination with any other term, refers to a straight-chain or branched-chain hydrocarbon radical having one or more triple bonds containing the specified number of carbon atoms, or where no number is specified, preferably from 2 to about 10 carbon atoms. Examples of alkynyl radicals include, but are not limited to, ethynyl, propynyl, propargyl, butynyl, pentynyl and the like.

The term "alkoxy" refers to an alkyl ether radical, wherein the term "alkyl" is defined above. Examples of suitable alkyl ether radicals include, but are not limited to, methoxy, ethoxy, n-propoxy, isopropoxy, n-butoxy, isobutoxy, sec-butoxy, tert-butoxy and the like.

The term "aryl," alone or in combination with any other term, refers to a carbocyclic aromatic radical (such as phenyl or naphthyl) containing the specified number of carbon atoms, preferably from 6–15 carbon atoms, and more preferably from 6–10 carbon atoms, optionally substituted with one or more substituents selected from alkyl, alkoxy, (for example methoxy), nitro, halogen, (for example chloro), amino, carboxylate and hydroxy. Examples of aryl radicals include, but are not limited to phenyl, p-tolyl, 4-hydroxyphenyl, 1-naphthyl, 2-naphthyl, indenyl, indanyl, azulenyl, fluorenyl, anthracenyl and the like.

The term "aralkyl", alone or in combination, means an alkyl radical as defined above in which one hydrogen atom is phenyl, benzyl, 2-phenylethyl and the like.

The term "aralkoxy carbonyl", alone or in combination, means a radical of the formula —C(O)—O-aralkyl in which the term "aralkyl" has the significance given above. An example of an aralkoxycarbonyl radical is benzyloxycarbonyl.

The term "aryloxy", alone or in combination, means a radical of the formula aryl-O— in which the term "aryl" has the significance given above.

The term "alkanoyl", alone or in combination, means an acyl radical derived from an alkanecarboxylic acid, examples of which include acetyl, propionyl, butyryl, valeryl, 4-methylvaleryl, and the like.

The term "aryloxyalkanoyl" means an acyl radical of the formula aryl-O— alkanoyl wherein aryl and alkanoyl have the significance given above.

The term "aralkanoyl" means an acyl radical derived from an aryl-substituted alkanecarboxylic acid such as phenylacetyl, 3-phenylpropionyl (hydrocinnamoyl), 4-phenylbutyryl, (2-naphthyl)acetyl, 4-chlorohydrocinnamoyl, 4-aminohydrocinnamoyl, 4-phenylbutyryl, (1-naphthyl)acetyl, 4-chlorohydrocinnamoyl, 4-aminohydrocinnamoyl, 4-methoxyhydrocinnamoyl, and the like.

The term "aroyl" means an acyl radical derived from an aromatic carboxylic acid. Examples of such radicals include aromatic carboxylic acids, an optionally substituted benzoic or naphthoic acid such as benzoyl, 4-chlorobenzoyl, 4-carboxybenzoyl, 4-benzyloxycarbonyl)benzoyl, 1-naphthoyl, 2-naphthoyl, 6-carboxy-2-naphthoyl, 6-(benzyloxycarbonyl)-2-naphthoyl, 3-benzyloxy-2-naphthoyl, 3-hydroxy-2-naphthoyl, 3-(benzyloxyformamido)-2-naphthoyl, and the like.

The term "aminocarbonyl" alone or in combination, means an amino-substituted carbonyl (carbamoyl) group derived from an amino-substituted carboxylic acid wherein the amino group can be a primary, secondary or tertiary amino group continuing substituents selected from hydrogen, alkyl, aryl, aralkyl, cycloalkyl, cycloalkylalkyl radicals and the like.

The term "aminoalkanoyl" means an acyl radical derived from an amino substituted alkanecarboxylic acid wherein the amino group can be a primary, secondary or tertiary amino group containing substituents selected from the group consisting of hydrogen, cycloalkyl, cycloalkylalkyl radicals and the like, examples of which include N,N-dimethylaminoacetyl and N-benzylaminoacetyl.

The term "carbocycle" refers to a non-aromatic stable 3- to 8-membered carbon ring which may be saturated, mono-unsaturated or poly-unsaturated. The carbocycle may be attached at any endocyclic carbon atom which results in a stable structure. Preferred carbocycles have 5–7 carbons.

The term "cycloalkyl", alone or in combination, means an alkyl radical which contains from about 3 to about 8 carbon atoms and is cyclic. Examples of such cycloalkyl radicals include cyclopropyl, cyclobutyl, cyclopentyl, cyclohexyl and the like.

The term "cycloalkylalkyl" means an alkyl radical as defined above which is substituted by a cycloalkyl radical containing from about 3 to about 8, preferably from about 3 to about 6, carbon atoms.

The term "cycloalkylcarbonyl" means an acyl group derived from a monocyclic or bridged cycloalkanecarboxylic acid such as cyclopropanecarbonyl, cyclohexanecarbonyl, adamantanecarbonyl, and the like, or from a benz-fused monocyclic cycloalkanecarboxylic acid which is optionally substituted by, for example, alkanoylamino, such as 1,2,3,4-tetrahydro-2-naphthoyl, 2-acetamido-1,2,3,4-tetrahydro-2-naphthoyl.

The term "cycloalkylalkoxycarbonyl" means an acyl group derived from a cycloalkylalkoxycarboxylic acid of the formula cycloalkylalkyl-O—COOH wherein cycloalkylalkyl has the significance given above.

The term "heterocyclyl" or "heterocycle" refers to a stable 3–7 membered monocyclic heterocyclic ring or 8–11 membered bicyclic heterocyclic ring which is either saturated or partially unsaturated, and which may be optionally benzo-fused if monocyclic and which is optionally substituted on one or more carbon atoms by halogen alkyl, alkoxy, oxo, and the like, and/or on a secondary nitrogen atom (i.e., –NH—) by alkyl, aralkoxycarbonyl, alkanoyl, phenyl or phenylalkyl or on a tertiary nitrogen atom (i.e., +N—) by oxido and which is attached via a carbon atom. Each heterocycle consists of one or more carbon atoms and from one to four heteroatoms selected from the group consisting of nitrogen, oxygen and sulfur. As used herein, the terms "nitrogen and sulfur heteroatoms" include any oxidized form of nitrogen and sulfur, and the quaternized form of any basic nitrogen. A heterocyclyl radical may be attached at any endocyclic carbon or heteroatom which results in the creation of a stable structure. Preferred heterocycles include 5–7 membered monocyclic heterocycles and 8–10 membered bicyclic heterocycles. Examples of such groups imidazolinoyl, imidazolidinyl, indazolinolyl, perhydropyridazyl, pyrrolinyl, pyrrolidinyl, piperidinyl, pyrazolinyl, piperazinyl, morpholinyl, thiamorpholinyl, thiazolidinyl, thiamorpholinyl sulfone, oxopiperidinyl, oxopyrrolidinyl, oxoazepinyl, tetrahydropyranyl, tetrahydrofuranyl, dioxolyl, dioxinyl, benzodioxolyl, dithiolyl, tetrahydrothienyl, sulfolanyl, dioxanyl, dioxolanyl, tetrahydrofurodihydrofuranyl, tetrahydropyranodihydrofuranyl, dihydropyranyl, tetradyrofurofuranyl and tetrahydropyranofuranyl.

The term heteroaryl refers to a stable 5–6 membered monocyclic or 8–11 membered bicyclic aromatic heterocycles where heterocycles is as defined above. Examples of such groups include imidazolyl, quinolyl, isoqinolyl, indolyl, indazolyl, pyridazyl, pyridyl, pyrrolyl, pyrazolyl, pyrazinyl, quinoxolyl, pyranyl, pyrimidinyl, furyl, thienyl, triazolyl, thiazolyl, carbolinyl, tetrazolyl, benzofuranoyl, thiamorpholinyl sulfone, oxazolyl, benzoxazolyl, benzimidazolyl, benzthiazolyl, oxopiperidinyl, oxopyrrolidinyl, oxoazepinyl, azepinyl, isoxozolyl, isothiazolyl, furazanyl, thiazolyl, thiadiazoyl, oxathiolyl.

The term "heterocyclylalkanoyl" is an acyl radical derived from a heterocyclyl-substituted alkane carboxylic acid wherein heterocyclyl has the significance given above.

The term "heterocyclyloxycarbonyl" means an acyl group derived from heterocyclyl-O—COOH wherein heterocyclyl is as defined above.

The term "heterocyclylalkoxycarbonyl" means an acyl radical derived from heterocyclyl-substituted alkane-O—COOH wherein heterocyclyl has the significance given above.

The term "heteroaryloxycarbonyl" means an acylradical derived from a carboxylic acid represented by heteroaryl-O—COOH wherein heteroaryl has the significance given above.

The term "halogen" means fluorine, chlorine, bromine or iodine.

The term haloalkyl means an alkyl with one or more of its hydrogens replaced by halogens.

The term "thioalkyl" means an alkyl radical having at least one sulfur atom, wherein alkyl has the significance given above. An example of a thioalkyl is $CH_3SCH_3$. The corresponding sulfoxide and sulfone of this thioalkyl $CH_3S(O)CH_3$ and $CH_3S(O)_2CH_3$ respectively. Unless expressly stated to the contrary, the terms "—$SO_2$—" and "—$S(O)_2$—" as used herein refer to a sulfone or sulfone derivative (i.e., both appended groups linked to the S), and not a sulfinate ester.

The term "substituted", whether preceded by the term "optionally" or not, and substitutions contained in formulas of this invention, refer to the replacement of one or more hydrogen radicals in a given structure with the radical of a specified substituent. When more than one position in a given structure may be substituted with more than one substituent selected from a specified group, the substituents may be either the same or different at every position (for example, the moiety —N(R2)(R2)). Typically, when a structure may be optionally substituted, 0–3 substitutions are preferred, and 0–1 substitutions is more preferred. Most preferred substituents are those which enhance protease inhibitory activity or intracellular antiviral activity in permissive mammalian cells or immortalized mammalian cell lines, or which enhance deliverability by enhancing solubility characteristics or enhancing pharmacokinetic or pharmacodynamic profiles as compared to the unsubstituted compound. Combinations of substituents and variables envisioned by this invention are only those that result in the formation of stable compounds. The term "stable", as used herein, refers to compounds which possess stability sufficient to allow manufacture and administration to a mammal by methods known in the art. Typically, such compounds are stable at a temperature of 40° C. or less, in the absence of moisture or other chemically reactive conditions, for at least a week.

This invention also envisions the quaternization of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

As used herein, the compounds of this invention, including the compounds of formula I are defined to include pharmaceutically acceptable derivatives or prodrugs thereof. A "pharmaceutically acceptable derivative or prodrug" means any pharmaceutically acceptable salt, ester, salt of an ester, or other derivative of a compound of this invention which, upon administration to a recipient, is capable of providing (directly or indirectly) a compound of this invention or an inhibitorily active metabolite or residue thereof. Particularly favored derivatives and prodrugs are those that increase the bioavailability of the compounds of this invention when such compounds are administered to a mammal (e.g., by allowing an orally administered compound to be more readily absorbed into the blood) or which enhance delivery of the parent compound to a biological compartment (e.g., the brain or lymphatic system) relative to the parent species.

Salts derived from appropriate bases include alkali metal (e.g., sodium), alkaline earth metal (e.g., magnesium), ammonium and N-$(C_{1-4}alkyl)_4^+$ salts.

The compounds of this invention contain one or more asymmetric carbon atoms and thus occur as racemates and racemic mixtures, single enantiomers, diastereomeric mixtures and individual diastereomers. All such isomeric forms of these compounds are expressly included in the present invention. Each stereogenic carbon may be of the R or S configuration. Although the specific compounds exemplified in this application may be depicted in a particular stereochemical configuration, compounds having either the opposite stereochemistry at any given chiral center or mixtures thereof are also envisioned.

The compounds of the present invention may be used in the form of pharmaceutically acceptable salts derived from inorganic or organic acids. Included among such acid salts, for example, are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate and undecanoate.

The instant compounds may be easily prepared according to those synthetic methods set forth in U.S. Pat. No. 6,319,946 to Hale et al., the disclosure of which is incorporated herein by reference in its entirety. These methods will be evident to those of ordinary skill in the art.

The following scheme may be followed to synthesize the instant compounds where the X substituent can be being varied. In this scheme P is a standard amine protecting group such as Boc or Cbz. The amine is reacted with the epoxide as described previously (J. Med. Chem. 36, 288–291 (93)). The resulting aminoalcohol is reacted with an activated sulfonic acid derivative where X is a leaving group such as halo, an activated alcohol, or a sulfonate. The protecting group is then removed from 3 and the resulting amino alcohol 4 is reacted with an activated oxycarbonyl derivative 5 (where Y is a leaving group such as halo or an activated alcohol) to give target compound 6. Compound 5 is generated from the corresponding alcohol by reacting with an acid chloride or an activated ester under standard conditions and is either isolated or used in situ.

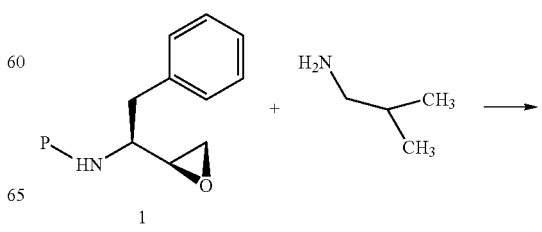

1

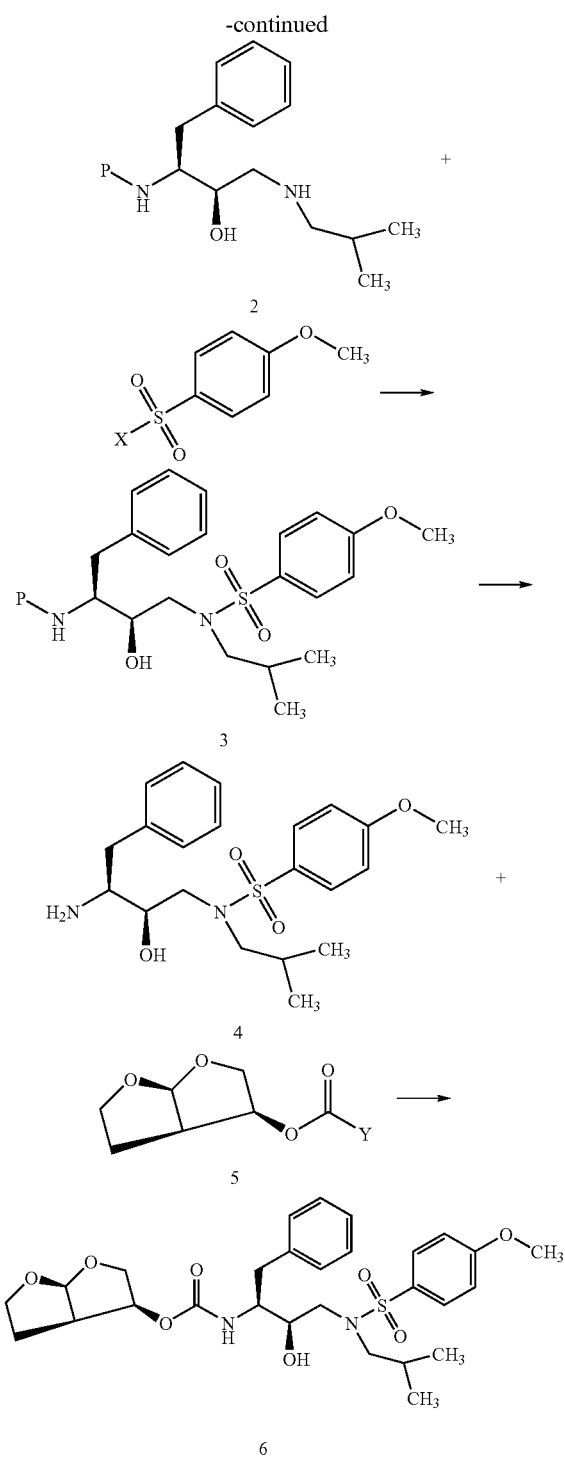

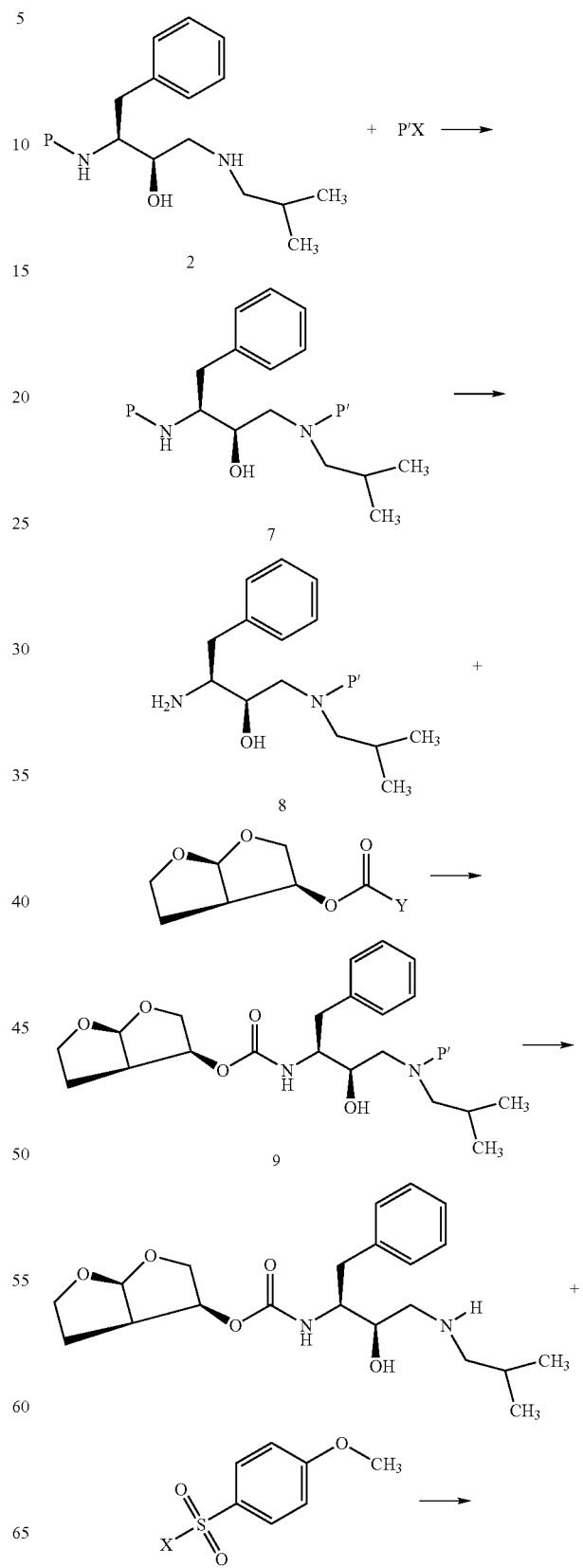

deprotection of 9 various X' groups may be introduced via the activated sulfonyl derivatives in a similar fashion as described above.

A diprotected amino epoxide such as (N,N-dibenzyl) may also be used as can an azido group that will eventually be reduced to an amine. In certain examples the activated sulfonyl derivative may be reacted with the amine and the resulting sulfonamide reacted with the epoxide under basic conditions.

A second representative synthesis can be used when exploring variations of X'. Here instead of being sulfonylated, amino alcohol 2 can be N-protected by a group that is not removed by removing P, for example P is Boc and P' is Carbobenzyloxy. The di-protected 7 is then deprotected to give 8 which is reacted as above to give 9. Following

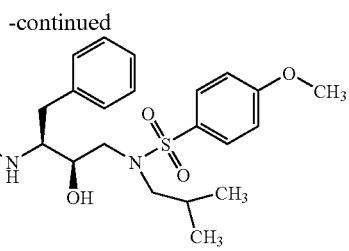

An example of a synthesis of X with a third fused ring is shown below. This olefinic tricyclic system has already been described by McElvain, et al. *JACS* 77, 5601 (1955). Anti-Markownikov addition of water across the double bond using standard conditions can provide the target alcohol. It is noteworthy that these authors showed that the unsubstituted tricyclic system had unusual acid stability, which may help prolong the activity of our target compounds.

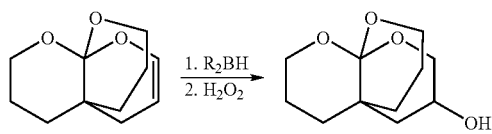

The synthesis of a bicyclo[2.2.0] system can proceed in a similar fashion as has been described Padias, et al. *J.O.C.* 52, 5305 (1987) for a homologous analog. R can either be H or a protecting group such as benzyl that can subsequently be removed under standard conditions. Protic (e.g. toluenesulfonic) or Lewis (e.g. scandium triflate) acids can be used for the condensation.

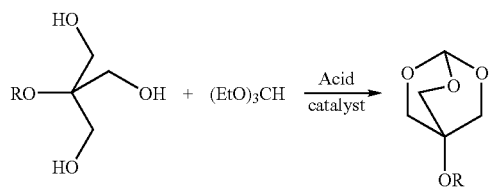

The synthesis of a representative phosphorus containing bicycle described herein. Similar chemistry has been described by Arnold, et al. *In Ang. Chem* 70, 539 (1958) and Dankiewicz, et al. in *JACS* 101, 7712 (1979). The R group in the target shown may either be H or a protecting group such as benzyl that can subsequently be removed.

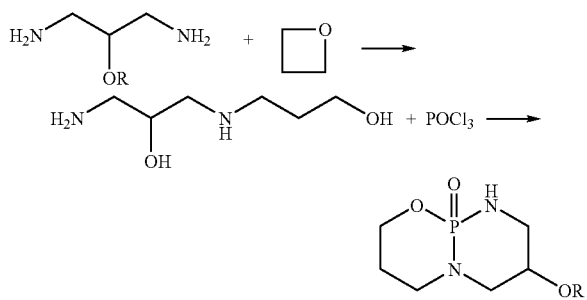

Other pharmaceutically acceptable salts include a salt with an inorganic base, organic base, inorganic acid, organic acid, or basic or acidic amino acid. Inorganic bases which form the instant pharmaceutically acceptable salts include alkali metals such as sodium or potassium, alkali earth metals such as calcium and magnesium or aluminum, and ammonia. Organic bases which form the instant pharmaceutically acceptable salts include trimethylamine, triethylamine, pyridine, picoline, ethanolamine, diethanolamine, triethanolamine, dicyclohexylamine. Inorganic acids which form the instant pharmaceutically acceptable salts include hydrochloric acid, hydroboric acid, nitric acid, sulfuric acid, and phosphoric acid. Organic acids appropriate to form the salt include formic acid, acetic acid, trifluoroacetic acid, fumaric acid, oxalic acid, tartaric acid, maleic acid, citric acid, succinic acid, malic acid, methanesulfonic acid, benzenesulfonic acid, and p-toluenesulfonic acid. Basic amino acids to form the salt include arginine, lysine and ornithine. Acidic amino acids to form the salt include aspartic acid and glutamic acid.

The instant invention also contemplates compositions which can be administered orally or non-orally in the form of, for example, granules, powders, tablets, capsules, syrup, suppositories, injections, emulsions, elixir, suspensions or solutions, by mixing these effective components, individually or simultaneously, with pharmaceutically acceptable carriers, excipients, binders, diluents or the like.

The compounds of the present invention-are useful in the treatment of individuals infected by HIV and for the prophylaxis of these individuals. The present invention may be useful in the treatment of mammals infected with viruses whose existence is mediated by, or depends upon, the protease enzyme. Conditions which may be prevented or treated with the compounds of the present invention, especially conditions associated with HIV and other pathogenic retroviruses, include AIDS, AIDS-related complex (ARC), progressive generalized lymphadenopathy (POL), as well as chronic CNS diseases caused by retroviruses, such as, for example HIV-mediated dementia and multiple sclerosis.

As a solid formulation for oral administration, the instant composition may be in the form of powders, granules, tablets, pills and capsules. In these cases, the instant compounds can be mixed with at least one additive, for example, sucrose, lactose, cellulose sugar, mannitol, maltitol, dextran, starch, agar, alginates, chitins, chitosans, pectins, tragacanth gum, gum arabic, gelatins, collagens, casein, albumin, synthetic or semi-synthetic polymers or glycerides. These formulations can contain, as in conventional cases, further additives, for example, an inactive diluent, a lubricant such as magnesium stearate, a preservative such as paraben or sorbic acid, an anti-oxidant such as ascorbic acid, tocopherol or cysteine, a disintegrator, a binder, a thickening agent, a buffer, a sweetener, a flavoring agent and a perfuming agent. Tablets and pills can further be prepared with enteric coating.

As used herein, "non-orally" includes subcutaneous injection, intravenous injection, intramuscular injections, intraperitoneal injection or instillation. Injectable preparations, for example, sterile injectable aqueous suspensions or oil suspensions can be prepared by known procedures in the fields concerned, using a suitable dispersant or wetting agent and suspending agent. The sterile injections may be, for example, a solution or a suspension, which is prepared with a non-toxic diluent administrable non-orally, such as an aqueous solution, or with a solvent employable for sterile injection. Examples of usable vehicles or acceptable solvents include water, Ringer's solution and an isotonic aqueous saline solution. Further, a sterile non-volatile oil can usually be employed as solvent or suspending agent. A non-volatile oil and a fatty acid can be used for this purpose, including natural or synthetic or semi-synthetic fatty acid oil or fatty acid, and natural or synthetic mono- or di- or tri-glycerides.

The instant pharmaceutical compositions may be formulated for nasal aerosol or inhalation and may be prepared as solutions in saline, and benzyl alcohol or other suitable preservatives, absorption promoters, fluorocarbons, or solubilizing or dispersing agents.

Rectal suppositories can be prepared by mixing the drug with a suitable vehicle, for example, cocoa butter and polyethylene glycol, which is in the solid state at ordinary temperatures, in the liquid state at temperatures in intestinal tubes and melts to release the drug.

Examples of liquid preparations for oral administration include pharmaceutically acceptable emulsions, syrups, elixirs, suspensions and solutions, which may contain an inactive diluent, for example, water.

The pharmaceutical composition may be easily formulated for topical administration with a suitable ointment containing one or more of the instant compounds suspended or dissolved in a carrier, which include, mineral oil, liquid petroleum, white petroleum, propylene glycol, polyoxyethylene polyoxypropylene compound, emulsifying wax and water. In addition, topical formulations can be formulated with a lotion or cream containing the active compound suspended or dissolved in a carrier. Suitable carriers include mineral oil, sorbitan monostearate, polysorbate 60, cetyl esters wax, cetearyl alcohol, 2-octyldodecanol, benzyl alcohol and water.

Dosages of the instant compounds are dependent on age, body weight, general health conditions, sex, diet, dose interval, administration routes, excretion rate, combinations of drugs and conditions of the diseases treated, while taking these and other necessary factors into consideration. Generally, dosage levels of between about 10 µg per day to about 5000 mg per day, preferably between about 100 mg per day to about 1000 mg per day of the compound are useful in the prevention and treatment of viral infection, including HIV infection. Typically, the pharmaceutical compositions of this invention will be administered from about 1 to about 5 times per day or alternatively, as a continuous infusion. Such administration can be used as a chronic or acute therapy.

The amount of active ingredient that may be combined with the carrier materials to produce a single dosage form will vary depending upon the host treated and the particular mode of administration. A typical preparation will contain from about 5% to about 95% active compound (w/w). Preferably, such preparations contain from about 20% to about 80% active compound.

While these dosage ranges can be adjusted by a necessary unit base for dividing a daily dose, as described above, such doses are decided depending on the diseases to be treated, conditions of such diseases, the age, body weight, general health conditions, sex, diet of the patient then treated, dose intervals, administration routes, excretion rate, and combinations of drugs, while taking these and other necessary factors into consideration. For example, a typical preparation will contain from about 0.05% to about 95% active compound (w/w). Preferably, such preparations contain from about 10% to about 80% active compound. The desired unit dose of the composition of this invention is administered once or multiple times daily.

Accordingly, a preferred embodiment the instant invention also contemplates compositions and formulations comprising one or more of the instant compounds in combination with one or more other HIV protease inhibitors, reverse transcriptase inhibitors, or non-nucleoside reverse transcriptase inhibitors.

The compounds of this invention may be administered to an uninfected or HIV-infected patient either as a single agent or in combination therapy with other anti-viral agents which interfere with the replication cycle of HIV in order to increase the therapeutic effect of these compounds. Thus, the present invention also relates to a compositions comprising a compound of the present invention, and another antiretroviral compound as a combined preparation for simultaneous, separate or sequential use in treatment of retroviral infections, in particular, in the treatment of infections with multi-drug resistant retroviruses. Thus, to combat or treat HIV infections, or the infection and disease associated with HIV infections, such as Acquired Immunodeficiency Syndrome (ADS) or, AIDS Related Complex (ARC), the compounds of this invention may be co-administered in combination with for instance, binding inhibitors, such as, for example, dextran sulfate, suramine, polyanions, soluble CD4, PRO-542, BMS-806; fusion inhibitors, such as, for example, T20, T1249, 5-helix, D-peptide ADS-Ji; co-receptor binding inhibitors, such as, for example, AMD 3100, AMD-3465, AMD7049, AMD3451 (Bicyclams), TAK 779; SHC-C(SCH351125), SHC-D, PRO-140RT inhibitors, such as, for example, foscamet and prodrugs; nucleoside RTIs, such as, for example, AZT, 3TC, DDC, DDI, D4T, Abacavir, FTC, DAPD, dOTC, DPC 817; nucleotide RTIs, such as, for example, PMEA, PMPA (tenofovir); NNRTIs, such as, for example, nevirapine, delavirdine, efavirenz, 8 and 9-Cl TIBO (tivirapine), loviride, TMC-125, dapivirine, MKC-442, UC 781, UC 782, Capravirine, DPC 961, DPC963, DPCO82, DPC083, calanolide A, SJ-1366, TSAO, 4"-deaminated TSAO, MV150, MV026048; RNAse H inhibitors, such as, for example, SPI093V, PD126338; TAT inhibitors, such as, for example, RO-5-3335, K12, K37; integrase inhibitors, such as, for example, L 708906, L 731988, S-1360; protease inhibitors, such as, for example, amprenavir and prodrug GW908, ritonavir, nelfinavir, saquinavir, indinavir, lopinavir, palinavir, BMS 186316, atazanavir, DPC 681, DPC 684, tipranavir, AG1776, mozenavir, GS3333, KNI-413, KNI-272, L754394, L756425, LG-71350, PD161374, PD173606, PD177298, PD178390, PD178392, PNU 140135, TMC114 maslinic acid, U-140690; glycosylation inhibitors, such as, for example, castanospermine, deoxynojirimycine.

The combination may in some cases provide a synergistic effect, whereby viral infectivity and its associated symptoms may be prevented, substantially reduced, or eliminated completely.

The compounds of the present invention may also be administered in combination with immunomodulators (e.g., bropirimine, anti-human alpha interferon antibody, IL-2, methionine enkephalin, interferon alpha, HE-2000 and naltrexone) with antibiotics (e.g., pentamidine isothiorate) cytokines (e.g. Th2), modulators of cytokines, chemokines or the receptors thereof (e.g. CCR5) or hormones (e.g. growth hormone) to ameliorate, combat, or eliminate HIM infection and its symptoms.

Such combination therapy in different formulations, may be administered simultaneously, separately or sequentially. Alternatively, such combination may be administered as a single formulation, whereby the active ingredients are released from the formulation simultaneously or separately.

The compounds of the present invention may also be administered in combination with modulators of the metabolization following application of the drug to an individual. These modulators include compounds that interfere with the metabolization at cytochromes, such as cytochrome P450. Some modulators inhibit cytochrome P450. It is known that several isoenzymes exist of cytochrome P450, one of which is cytochrome P450 3A4. Ritonavir is an example of a modulator of inetabolization via cytoclirome P450. Such combination therapy in different formulations, may be administered simultaneously, separately or sequentially. Alternatively, such combination maybe administered as a single formulation, whereby the active ingredients are released from the formulation simultaneously or separately. Such modulator may be administered at the same or different ratio as the compound of the present invention. Preferably, the weight ratio of such modulator vs. a compound of the present invention (modulator:compound of the presentinvention) is 1:1 or lower, more preferable the ratio is 1:3 or lower, suitably the ratio is 1:10 or lower, more suitably the ratio is 1:30 or lower.

In order to enhance the solubility and/or the stability of the compounds of formula I in pharmaceutical compositions, α, β, or γ cyclodextrins or their derivatives may be emplyed. Also co-solvents such as alcohols may improve the solubility and/or the stability of the compounds of formula I in pharmaceutical compositions. In the preparation of aqueous compositions, addition salts of the subject compounds may be more suitable due to their increased water solubility.

Appropriate cyclodextrins are α, β, or γ-cyclodextrins (CDs) or ethers and mixed ethers thereof wherein one or more of the hydroxy groups of the anhydroglucose units of the cyclodextrin are substituted with C1–C6alkyl, such as methyl, ethyl or isopropyl, e.g. randomly methylated β-CD; hydroxy C16 alkyl, particularly hydroxy-ethyl, hydroxypropyl or hydroxybutyl; carboxy C1–C6alkyl, particularly carboxymethyl or carboxyethyl; C1–C6alkyl-carbonyl, particularly acetyl; C1–C6 alkyloxycarbonylC1–C6alkyl or carboxyC16alkyloxyC1–C6alkyl, particularly carboxymethoxypropyl or carboxyethoxypropyl; C1–C6alkylcarbonyloxyC1–C6alkyl, particularly 2-acetyloxypropyl. Especially noteworthy as complexants and/or solubilizers are β-CD, randomly methylated β-CD, 2,6-dimethyl-β-CD, 2-hydroxyethyl-β-CD, 2-hydroxyethyl-γ-CD, hydroxy-propyl-γ-CD and (2-carboxymethoxy)propyl-β-CD, and in particular 2-hydroxy-propyl-β-CD (2-HP-β-CD).

The term mixed ether denotes cyclodextrin derivatives wherein at least two cyclodextrin hydroxy groups are etherified with different groups such as, for example, hydroxypropyl and hydroxyethyl.

The present compounds may be formulated in combination with a cyclodextrin or a derivative thereof as described in EP-A-721,331. Although the formulations described therein are with antifungal active ingredients, they are equally relevant for formulating compounds of the present invention. The formulations described therein are particularly suitable for oral administration and comprise an antifungal as active ingredient, a sufficient amount of a cyclodextrin or a derivative thereof as a solubilizer, an aqueous acidic medium as bulk liquid carrier and an alcoholic co-solvent that greatly simplifies the preparation of the composition. The formulations may also be rendered more palatable by adding pharmaceutically acceptable sweeteners and/or favors.

Other convenient ways to enhance the solubility of the compounds of the present invention in pharmaceutical compositions are described in WO 94/05263, WO 98/42318, EP-A-499,299 and WO 97/44014, all incorporated herein by reference.

More in particular, the present compounds may be formulated in a pharmaceutical composition comprising a therapeutically effective amount of particles consisting of a solid dispersion comprising a compound of formula I, and one or more pharmaceutically acceptable water-soluble polymers.

The term "a solid dispersion" defines a system in a solid state comprising at least two components, wherein one component is dispersed more or less evenly throughout the other component or components. When said dispersion of the components is such that the system is chemically and physically uniform or homogenous throughout or consists of one phase as defined in thermodynamics, such a solid dispersion is referred to as "a solid solution". Solid solutions are prefered physical systems because the components therein are usually readily bioavailable to the organisms to which they are administered.

The term "a solid dispersion" also comprises dispersions which are less homogenous throughout than solid solutions. Such dispersions are not chemically and physically uniform throughout or comprise more than one phase.

The water-soluble polymer in the particles is conveniently a polymer that has an apparent viscosity of 1 to 100 mPa.s when dissolved in a 2% aqueous solution at 20° C.

Preferred water-soluble polymers are hydroxypropyl methylcelluloses (HPMC). HPMC having a methoxy degree of substitution from about 0.8 to about 2.5 and a hydroxypropyl molar substitution from about 0.05 to about 3.0 are generally water soluble. Methoxy degree of substitution refers to the average number of methyl ether groups present per anhydroglucose unit of the cellulose molecule. Hydroxypropyl molar substitution refers to the average number of moles of propylene oxide which have reacted with each anhydroglucose unit of the cellulose molecule.

The particles as defined hereinabove can be prepared by first preparing a solid dispersion of the components, and then optionally grinding or milling that dispersion. Marious techniques exist for preparing solid dispersions including melt-extrusion, spray-drying and solution-evaporation.

It may further be convenient to formulate the present compounds in the form of nanoparticles which have a surface modifier adsorbed on the surface thereof in an amount sufficient to maintain an effective average particle size of less than 1000 nm. Useful surface modifiers are believed to include those which physically adhere to the surface of the antiretroviral agent but do not chemically bond to the antiretroviral agent.

Suitable surface modifiers can preferably be selected from known organic and inorganic pharmaceutical excipients. Such excipients include various polymers, low molecular weight oligomers, natural products and surfactants. Preferred surface modifiers include nonionic and anionic surfactants.

The present compounds may also be incorporated in hydrophilic polymers and applied as a film over many small beads, thus yielding a composition with good bioavailability which can conveniently be manufactured and which is suitable for preparing pharmaceutical dosage forms for oral administration. The beads comprise a central, rounded or spherical core, a coating film of a hydrophilic polymer and an antiretroviral agent and a seal-coating polymer layer. Materials suitable for use as cores are pharmaceutically acceptable and have appropriate dimensions and firmness. Examples of such materials are polymers, inorganic substances, organic substances, saccharides and derivatives thereof. The route of administration may depend on the condition of the subject, co-medication and the like.

The instant compounds and compositions retain inhibitory activity, or potency, over a broad spectrum of related but non-identical retroviral proteases. Accordingly, in another preferred embodiment, the instant invention includes methods for treating or preventing viral infections. Treating or preventing refers to alleviating or hindering symptoms or effects of a viral infection in an infected animal, such as a mammal, particularly a human. Treating includes prophylaxis as well as the treatment of viral infections or symptoms of viral infections. The instant methods comprise treating an animal with a therapeutically effective amount of a compound or composition according to the instant invention. According to a preferred embodiment, the viral infection is an HIV infection, preferably an mdrHIV infection.

Moreover, the instant compounds and compositions are particularly effective as inhibitors against drug resistant and mdrHIV strains and multi-drug resistant HIV proteases (mdrPR). Accordingly, in another preferred embodiment, the instant invention provides methods for inhibiting HIV protease, particularly drug resistant and multi-drug resistant HIV proteases (mdrPR), with a therapeutically effective amount of a compound or composition according to the instant invention.

In relation to the above, the instant compounds may be used in vaccines for protecting individuals against viral, specifically, mdrHIV infections. As such, the instant compounds may be employed as protease inhibitors as conventionally used in vaccines. In this regard, one or more of the instant compounds may be combined with a pharmaceutically acceptable adjuvant conventionally employed in vaccines and administered in prophylactically effective amounts to protect individuals over an extended period time against HIV infection.

The present invention also relates to a novel compositions and a methods for improving the pharmacokinetics of drugs which are metabolized by cytochrome P450 monooxygenase. In addition, the present invention relates to a novel composition and a method for inhibiting retroviral proteases and in particular for inhibiting human immunodeficiency virus (HIV) protease and a composition and a method for inhibiting a retroviral infection, in particular an HIV infection.

In this connection, the present invention provides a method of improving the pharmacokinetics of a drug (or a pharmaceutically acceptable salt thereof) which is metabolized by cytochrome P450 monooxygenase comprising coadministering a compound of the instant invention or a pharmaceutically acceptable salt thereof. When administered in combination, the two therapeutic agents can be formulated as separate compositions which are administered at the same time or different times, or the two therapeutic agents can be administered as a single composition.

Drugs which are metabolized by cytochrome P450 monooxygenase and which benefit from coadministration with a compound of the instant invetion include, but are not limited to, ritonavir, the immunosuppressants cyclosporine, FK-506 and rapamycin, the chemotherapeutic agents taxol and taxotere, the antibiotic clarithromycin and the HIV protease inhibitors A-77003, A-80987, MK-639, saquinavir, VX-478, AG1343, DMP-323, XM-450, BILA 2011 BS, BILA 1096 BS, BILA 2185 BS, BMS 186,318, LB71262, SC-52151, SC-629 (N,N-dimethylglycyl-N-(2-hyrdoxy-3-(((4-methoxyphenyl)sulphonyl)(2-methylp ropyl)amino)-1-(phenylmethyl)propyl)-3-methyl-L-valinamide), KNI-272, CGP 53437, CGP 57813 and U-103017.

In a preferred embodiment of the present invention, there is disclosed a method for improving the pharmacokinetics of an HIV protease inhibitor (or a pharmaceutically acceptable salt thereof) which is metabolized by cytochrome P450 monooxygenase comprising coadministering a compound of the instant invention or a pharmaceutically acceptable salt thereof. Such a combination of a compound of the instant invention or a pharmaceutically acceptable salt thereof and an HIV protease inhibitor or a pharmaceutically acceptable salt thereof which is metabolized by cytochrome P450 monooxygenase is useful for inhibiting HIV protease in humans and is also useful for inhibition, treatment or prophylaxis of an HIV infection or AIDS (acquired immune deficiency syndrome) in humans. When administered in combination, the two therapeutic agents can be formulated as separate compositions which are administered at the same time or different times, or the two therapeutic agents can be administered as a single composition.

The following examples illustrate further the present invention but, of course, should not be construed in any way of limiting its scope.

EXAMPLES

Example 1

This example describes the antiviral activity, resistance profile, and selection of resistance mutations for a resistance-repellent PI (UIC-94003, FIG. 1; also referred to as compound 1, vide infra). Also described in this example is a preliminary analysis by computer modeling of the structural basis of the resistance-repellent properties of 1.

Compound 1 was originally identified as a potent protease inhibitor of multidrug drug resistant HIV mutants using a novel biochemical fitness profiling strategy described in Erickson and Gulnik, WO 99/67417, which application is included herein in its entirety. The biochemical resistance profile (Ki,mutant/Ki,wild type) and biochemical fitness, or vitality, profile (Ki,mutant/Ki,wild type×(kcat,mutant/Km, mutant)/(kcat,wild type/Km,wild type) of compound 1 is described in Table 1 in Example 13 (as Compound 32) of Erickson and Gulnik, vide supra. Antiviral potencies against wild type and multi-drug resistant HIV strains are described in Table 3 in Example 14 of Erickson and Gulnik, vide supra. Based on the biochemical fitness and antiviral drug resistance profiles, it was predicted that drug resistant viruses containing the characteristic mutations described in Erickson and Gulnik WO 99/67417 would not emerge from the wild type virus in the presence of 1. This prediction was largely borne out in the present example, which provides new data on the selection of mutations using compound 1, as well as additional biological and structural data related to the antiviral and resistance-repellent properties of compound 1. Data from the present example are described in detail in Yoshimura et al., *J. Virol.*, 76, 1349–1358 (2002).

In Vitro Drug Sensitivity of HIV-1 Laboratory Isolates to Compound 1 and other PIs The sensitivities of HIV-1$_{LAI}$, HIV-1$_{Ba-L}$, HIV-2$_{EHO}$ and the primary HIV-1 isolates against various drugs were determined as previously described with minor modifications (Shiraska et al., *Proc. Natl. Acad. Sci. USA*, 92, 2398–2402 (1995)). The antiviral activity of 1 was >10-fold more potent than any of the five currently available PIs against both HIV-1$_{LAI}$ and HIV-1$_{Ba-L}$ in PHA-PBMC (IC$_{50}$: 0.0003 µM) (Table 1).

In Vitro Activity of Compound 1 Against Highly PI-Resistant Clinical HIV-1 Strains Compound 1 was also active against highly cross-resistant HIV-1 strains derived from AIDS patients who had failed on 9 to 11 anti-HIV-1 drugs (Falloon et al., *Clin. Infect. Dis.*, 30, 313–318 (2000); Yoshimura et al., *Proc. Natl. Acad. Sci. USA*, 96, 8675–8680 (1999)). These HIV-1 strains contained up to fourteen amino acid substitutions in the protease-encoding region, and had high-level resistance to RTV, IDV, NFV and APV (6- to >77-fold), and moderate-to-high level resistance to SQV (3-31-fold), as compared to a wild-type clinical strain HIV-1$_{ERS104pre}$. In contrast, 1 suppressed the replication of all eight isolates with IC$_{50}$ values ranging 0.0005–0.0055 µM (Table 2). While two strains (strains 1 and 7) were 6- and 8-fold less susceptible to 1, the IC$_{50}$ values remained extremely low, 0.004 and 0.0055 µM, respectively (Table 2).

Generation of Compound 1-Resistant HIV-1 In Vitro.

Selection of HIV-1 variants resistant to Compound 1 and a structurally-related PI, amprenavir, was performed in vitro by propagating HIV-1$_{NL4-3}$ in MT-2 cells in the presence of increasing concentrations of drug as described in Yoshimura et al., (2002), vide supra. The virus required 32 passages to acquire a 100-fold increase in the highest compound 1 concentration at which the virus could propagate while it required only 21 passages for the virus to acquire the same level of resistance against amprenavir (FIG. 2). For the virus to acquire a 500-fold increase to compound 1, 46 passages were required, while 31 passages were required for viral acquisition of the same level of resistance against APV (FIG. 2).

Nucleotide sequencing of proviral DNAs from the lysates of infected cells was used to determine the mutations selected by each drug. Individual protease sequences and their frequency at each passage are depicted in FIG. 3. The wild-type protease gene sequence was seen in 8 of 8 clones derived from HIV-1$_{NL4-3}$ at passage 4 (HIV-1$_{UIC-P4}$). An A28S mutation at the active site of the enzyme was seen early (at passage 15) in 5 of 9 clones of HIV-1$_{UIC-P15}$, and it was subsequently seen consistently at frequencies of >50% (except 44% for HIV-1$_{P42}$), suggesting that this mutation was critical in conferring resistance to compound 1. A substitution at residue 50 from Ile to Val, seen in HIV-1 resistant to APV (8, 26), was also identified at passage 26 and beyond. It appeared that the I50V mutation brought about a significant change in protease since the virus started to replicate relatively rapidly in the presence of compound 1 following the emergence of I50V (FIG. 2). It is noteworthy that these two active site mutations, A28S and I50V, did not co-exist in any clones except in 3 clones throughout the selection (FIG. 3). Compensatory, non-active site mutations that were selected at later passages included L10F, M46I and A71V.

Sensitivity of Compound 1-Selected HIV-1 to Various PIs

Viruses at passage 62 with 2 µM 1 (HIV-1$_{UIC-P62}$) and those at passage 30 with 5 µM APV (HIV-1$_{APV-P30}$) were titrated, and their susceptibilities to 1, APV, and several other PIs were determined (Table 3). HIV-1$_{UIC-P62}$ was highly resistant to APV and 1 (IC$_{50}$ values were 20- and 70-fold greater than that of HIV-1$_{NL4-3}$, respectively). However, HIV-1$_{UIC-P62}$ was as sensitive to RTV and SQV as the parental HIV-1$_{NL4-3}$, while it was moderately resistant to IDV and NFV (7- and 5-fold increases in IC$_{50}$ values, respectively). In contrast, HIV-1$_{APV-P30}$ was highly resistant to all PIs tested except SQV (Table 3). These data suggest that 1 has significant advantages compared to APV in terms of the emergence of drug resistance: (i) the viral acquisition of resistance to 1 is substantially delayed (FIG. 2); (ii) 1 resistant HIV remains sensitive to all PIs except APV; and, (iii) in contrast, APV-resistant virus is highly cross-resistant to all PIs, except SQV (Table 3).

Molecular Modeling of Interaction of HIV-1 Protease and Compound 1

A structural model of HIV-1 protease complexed, with Compound 1 was prepared based on the crystal structures of HIV-1 protease complexed with APV (Kim et al., J. Amer. Chem. Soc., 117, 1181 (1995)) and with compound 49 (Ghosh et al., J. Med. Chem., 37, 1506–2508). These two structures were chosen because Compound 1 is closely related in structure to APV, except for the presence of the P2 bis-THF moiety, which is contained in compound 49. FIG. 4 shows an optimized molecular model of the protease-1 complex, and illustrates the locations of amino acid residues where substitutions were identified in HIV-1$_{P62}$. Ile50 is located on the internal surface of the flap of HIV-1 protease from where its aliphatic side chain atoms making van der Waals contacts with inhibitor atoms. Ala28 is located between the conserved catalytic-triad, Asp25-Thr26-Gly27, and two major substrate and inhibitor binding residues, Asp29 and Asp30, but is not itself directly involved in binding. Met46 is located on the external surface of the flap of HIV protease. Ile10, Asn88, and Ala71 are located far from the active site of the enzyme. These mutations presumably improve the fitness of active site-containing mutants by exerting long-range effects on inhibitor or substrate binding, or by some other compensatory mechanism (Erickson and Burt, (1996) vide supra; Erickson et al., AIDS, (1999) vide supra).

The model also showed that, using the bound conformation of APV for compound 1, the two oxygen atoms of the bis-THF group of compound 1 could be positioned to form hydrogen bonds with the main chain amides of Asp29 and Asp30 in a manner similar to that observed previously for compound 49 (FIG. 5). In the model, compound 1 does not make any interactions with Ala28 (FIG. 5). This is consistent with the structure of the APV/protease complex, in which Ala28 also does not play a direct role in binding.

The high potency of Compound 1 relative to APV is consistent with previous studies that have shown an increase in potency when a THF group is replaced by a fused ring bis-THF moiety (Ghosh et al., Bioorg. Med. Chem. Lett., 8, 687–690 (1998); Ghosh et al., (1994), vide supra). The modeling analysis suggests that the increased potency appears to stem from the ability of the two, conformationally-constrained, ring oxygen atoms in the bis-THF group to form hydrogen bonds with the the main chain amide hydrogen atoms of Asp29 and Asp30 in the S2 subsite (FIG. 5). Since the main chain atoms cannot mutate, these interactions may be important for 1's broad spectrum of activity against multi-drug resistant variants.

No amino acid mutations were seen (except at early passages during the selection of HIV-1 with 1) at the two active site residues, Val82 and Ile84, whose side chains are involved in making direct contacts with all PIs. Mutations at these two active sites are commonly seen in HIV-1 resistant to various PIs. Mutations at Val82 are highly effective at conferring resistance and, when combined with a second active site mutation, such as V32I, can result in widespread biochemical cross-resistance to PIs. The Ile84 residue, along with the symmetry-related I84', makes interactions across S2/S1' and S1/S2' subsites, respectively, and the I84V mutation has been observed in clinical resistance with various PIs including RTV, IDV, SQV, and APV. HIV-1 propagated in the presence of compound 1 did not attain stable mutations at V82, and did not acquire those at I84V (except for one clone), indicating that the acquisition of resistance to this PI by wild type HIV-1 may require different evolutionary pathways than have been heretofore observed for most PIs.

The D30N mutation is a primary resistance mutation for nelfinavir, which forms a hydrogen bond with the side chain of Asp30). and has no effect on binding of compound 1. Consistent with these observations, HIV-1 exposed to 1 does not select mutations at codon 30.

Infectious clones containing either A28S or I50V in the pNL4-3 background replicated poorly compared to HIV-1$_{wt}$ in MT-2 cells (data not shown). In a published biochemical study, the A28S mutation in HIV protease caused a more than 1,500-fold decrease in $K_{cat}/K_m$ values for peptide substrates (Hong, et al., *Protein Sci.,* 7, 300–305 (1998)). These results suggest that, while the A28S mutation represents a critical mutation for resistance to 1, it confers a severe replication disadvantage on the virus.

When HIV-$1_{NL4-3}$ was propagated in the presence of increasing concentrations of 1 or APV, the appearance of HIV-1 strains that were highly resistant to 1 were delayed compared to the appearance of HIV-1 strains highly resistant to APV (FIG. 2). Taken together, the above data are consistent with the prediction that compound 1 is a "resistance-repellent" PI as defined above.

These data suggest that 1 and other compounds having the general structure described herein have at least four advantages: (i) they exert potent activity against a wide spectrum of drug-resistant HIV-1 variants presumably due to their interaction with the main chains of the active site amino acids (Asp29 and Asp30); and (ii) their unique contact with HIV-1 protease is different from that of other PIs; (iii) the viral acquisition of resistance is substantially delayed; and (iv) at least several PIs remain active in vitro against the virus selected in vitro with 1 or the other compounds (Table 3).

Example 2

This example illustrates the method by which experimentally-determined crystal structures of the same inhibitor in complex with wild type and mutant species of HIV protease can be compared and analyzed for the existence of a three-dimensionally conserved substructure.

The structures of wild type HIV-1 protease and a mutant, V82F/I84V, HIV-1 protease, both in complexes with the inhibitor shown in FIG. 1 were determined using conventional x-ray crystallography techniques. The structures were analyzed by means of (a) an overall superposition of the atoms of the protein structures; and, (b) a study of the distances from polar atoms of the inhibitors to polar atoms of the protein. This analysis requires three dimensional atomic coordinates of the protein structures and of the bound inhibitor.

The superposition of the protein structures was performed in a two step process: 1) the distance between all pairs of corresponding Cα atoms (Cα atom of residue number 1 in one protein to Cα atom of residue number 1 in the second protein; Cα atom of residue number 2 in one protein to Cα atom of residue number 2 in the second protein; and so on) of the polypeptide chains is minimized by means of a least-square algorithm; 2) the superposition is refined by minimizing, in an iterative process, the distances between corresponding Cα atoms that are closer than a given distance (0.25 Å in this example), thus eliminating regions of the structures having large conformational differences to compute the superposition parameters. The distances between equivalenced Cα atoms after the minimization procedure are shown in Table 4.

TABLE 4

Distances between equivalent Cα atoms

| Molecule 1 | | | Molecule 2 | | | distance [Å] |
|---|---|---|---|---|---|---|
| CA | PRO | 1 | CA | PRO | 1 | 0.455 |
| CA | GLN | 2 | CA | GLN | 2 | 0.434 |
| CA | ILE | 3 | CA | ILE | 3 | 0.418 |
| CA | THR | 4 | CA | THR | 4 | 0.317 |
| CA | LEU | 5 | CA | LEU | 5 | 0.172 |
| CA | TRP | 6 | CA | TRP | 6 | 0.228 |
| CA | GLN | 7 | CA | GLN | 7 | 0.364 |
| CA | ARG | 8 | CA | ARG | 8 | 0.166 |
| CA | PRO | 9 | CA | PRO | 9 | 0.057 |
| CA | LEU | 10 | CA | LEU | 10 | 0.183 |
| CA | VAL | 11 | CA | VAL | 11 | 0.194 |
| CA | THR | 12 | CA | THR | 12 | 0.168 |
| CA | ILE | 13 | CA | ILE | 13 | 0.146 |
| CA | LYS | 14 | CA | LYS | 14 | 0.229 |
| CA | ILE | 15 | CA | ILE | 15 | 0.266 |
| CA | GLY | 16 | CA | GLY | 16 | 0.662 |
| CA | GLY | 17 | CA | GLY | 17 | 0.491 |
| CA | GLN | 18 | CA | GLN | 18 | 0.267 |
| CA | LEU | 19 | CA | LEU | 19 | 0.112 |
| CA | LYS | 20 | CA | LYS | 20 | 0.128 |
| CA | GLU | 21 | CA | GLU | 21 | 0.190 |
| CA | ALA | 22 | CA | ALA | 22 | 0.169 |
| CA | LEU | 23 | CA | LEU | 23 | 0.218 |
| CA | LEU | 24 | CA | LEU | 24 | 0.233 |
| CA | ASP | 25 | CA | ASP | 25 | 0.160 |
| CA | THR | 26 | CA | THR | 26 | 0.200 |
| CA | GLY | 27 | CA | GLY | 27 | 0.303 |
| CA | ALA | 28 | CA | ALA | 28 | 0.169 |
| CA | ASP | 29 | CA | ASP | 29 | 0.150 |
| CA | ASP | 30 | CA | ASP | 30 | 0.038 |
| CA | THR | 31 | CA | THR | 31 | 0.047 |
| CA | VAL | 32 | CA | VAL | 32 | 0.173 |
| CA | LEU | 33 | CA | LEU | 33 | 0.194 |
| CA | GLU | 34 | CA | GLU | 34 | 0.310 |
| CA | GLU | 35 | CA | GLU | 35 | 0.260 |
| CA | MET | 36 | CA | MET | 36 | 0.136 |
| CA | SER | 37 | CA | SER | 37 | 0.494 |
| CA | LEU | 38 | CA | LEU | 38 | 0.607 |

TABLE 4-continued Distances between equivalent Cα atoms

| Molecule 1 | | | Molecule 2 | | | distance [Å] |
|---|---|---|---|---|---|---|
| CA | PRO | 39 | CA | PRO | 39 | 0.094 |
| CA | GLY | 40 | CA | GLY | 40 | 0.774 |
| CA | ARG | 41 | CA | ARG | 41 | 0.448 |
| CA | TRP | 42 | CA | TRP | 42 | 0.204 |
| CA | LYS | 43 | CA | LYS | 43 | 0.596 |
| CA | PRO | 44 | CA | PRO | 44 | 0.625 |
| CA | LYS | 45 | CA | LYS | 45 | 0.541 |
| CA | MET | 46 | CA | MET | 46 | 0.643 |
| CA | ILE | 47 | CA | ILE | 47 | 0.361 |
| CA | GLY | 48 | CA | GLY | 48 | 0.240 |
| CA | GLY | 49 | CA | GLY | 49 | 0.182 |
| CA | ILE | 50 | CA | ILE | 50 | 0.110 |
| CA | GLY | 51 | CA | GLY | 51 | 0.243 |
| CA | GLY | 52 | CA | GLY | 52 | 0.200 |
| CA | PHE | 53 | CA | PHE | 53 | 0.119 |
| CA | ILE | 54 | CA | ILE | 54 | 0.255 |
| CA | LYS | 55 | CA | LYS | 55 | 0.295 |
| CA | VAL | 56 | CA | VAL | 56 | 0.108 |
| CA | ARG | 57 | CA | ARG | 57 | 0.129 |
| CA | GLN | 58 | CA | GLN | 58 | 0.074 |
| CA | TYR | 59 | CA | TYR | 59 | 0.372 |
| CA | ASP | 60 | CA | ASP | 60 | 0.496 |
| CA | GLN | 61 | CA | GLN | 61 | 0.780 |
| CA | ILE | 62 | CA | ILE | 62 | 0.406 |
| CA | LEU | 63 | CA | LEU | 63 | 0.211 |
| CA | ILE | 64 | CA | ILE | 64 | 0.260 |
| CA | GLU | 65 | CA | GLU | 65 | 0.193 |
| CA | ILE | 66 | CA | ILE | 66 | 0.181 |
| CA | CYS | 67 | CA | CYS | 67 | 0.518 |
| CA | GLY | 68 | CA | GLY | 68 | 0.641 |
| CA | HIS | 69 | CA | HIS | 69 | 0.319 |
| CA | LYS | 70 | CA | LYS | 70 | 0.179 |
| CA | ALA | 71 | CA | ALA | 71 | 0.265 |
| CA | ILE | 72 | CA | ILE | 72 | 0.350 |
| CA | GLY | 73 | CA | GLY | 73 | 0.253 |
| CA | THR | 74 | CA | THR | 74 | 0.301 |
| CA | VAL | 75 | CA | VAL | 75 | 0.187 |
| CA | LEU | 76 | CA | LEU | 76 | 0.186 |
| CA | VAL | 77 | CA | VAL | 77 | 0.070 |
| CA | GLY | 78 | CA | GLY | 78 | 0.306 |
| CA | PRO | 79 | CA | PRO | 79 | 0.047 |
| CA | THR | 80 | CA | THR | 80 | 0.470 |
| CA | PRO | 81 | CA | PRO | 81 | 0.404 |
| CA | VAL | 82 | CA | PHE | 82 | 0.556 |
| CA | ASN | 83 | CA | ASN | 83 | 0.146 |
| CA | ILE | 84 | CA | VAL | 84 | 0.196 |
| CA | ILE | 85 | CA | ILE | 85 | 0.163 |
| CA | GLY | 86 | CA | GLY | 86 | 0.224 |
| CA | ARG | 87 | CA | ARG | 87 | 0.127 |
| CA | ASN | 88 | CA | ASN | 88 | 0.048 |
| CA | LEU | 89 | CA | LEU | 89 | 0.081 |
| CA | LEU | 90 | CA | LEU | 90 | 0.197 |
| CA | THR | 91 | CA | THR | 91 | 0.226 |
| CA | GLN | 92 | CA | GLN | 92 | 0.176 |
| CA | ILE | 93 | CA | ILE | 93 | 0.151 |
| CA | GLY | 94 | CA | GLY | 94 | 0.338 |
| CA | CYS | 95 | CA | CYS | 95 | 0.233 |
| CA | THR | 96 | CA | THR | 96 | 0.305 |
| CA | LEU | 97 | CA | LEU | 97 | 0.089 |
| CA | ASN | 98 | CA | ASN | 98 | 0.260 |
| CA | PHE | 99 | CA | PHE | 99 | 0.250 |
| CA | PRO | 101 | CA | PRO | 101 | 0.227 |
| CA | GLN | 102 | CA | GLN | 102 | 0.108 |
| CA | ILE | 103 | CA | ILE | 103 | 0.206 |
| CA | THR | 104 | CA | THR | 104 | 0.169 |
| CA | LEU | 105 | CA | LEU | 105 | 0.125 |
| CA | TRP | 106 | CA | TRP | 106 | 0.363 |
| CA | GLN | 107 | CA | GLN | 107 | 0.296 |
| CA | ARO | 108 | CA | ARG | 108 | 0.400 |
| CA | PRO | 109 | CA | PRO | 109 | 0.173 |
| CA | LEU | 110 | CA | LEU | 110 | 0.182 |
| CA | VAL | 111 | CA | VAL | 111 | 0.085 |
| CA | THR | 112 | CA | THR | 112 | 0.123 |
| CA | ILE | 113 | CA | ILE | 113 | 0.107 |
| CA | LYS | 114 | CA | LYS | 114 | 0.368 |

TABLE 4-continued

Distances between equivalent Cα atoms

| Molecule 1 | | | Molecule 2 | | | distance [Å] |
|---|---|---|---|---|---|---|
| CA | ILE | 115 | CA | ILE | 115 | 0.226 |
| CA | GLY | 116 | CA | GLY | 116 | 0.638 |
| CA | GLY | 117 | CA | GLY | 117 | 0.516 |
| CA | GLN | 118 | CA | GLN | 118 | 0.414 |
| CA | LEU | 119 | CA | LEU | 119 | 0.102 |
| CA | LYS | 120 | CA | LYS | 120 | 0.191 |
| CA | GLU | 121 | CA | GLU | 121 | 0.206 |
| CA | ALA | 122 | CA | ALA | 122 | 0.197 |
| CA | LEU | 123 | CA | LEU | 123 | 0.231 |
| CA | LEU | 124 | CA | LEU | 124 | 0.145 |
| CA | ASP | 125 | CA | ASP | 125 | 0.235 |
| CA | THR | 126 | CA | THR | 126 | 0.311 |
| CA | GLY | 127 | CA | GLY | 127 | 0.200 |
| CA | ALA | 128 | CA | ALA | 128 | 0.102 |
| CA | ASP | 129 | CA | ASP | 129 | 0.143 |
| CA | ASP | 130 | CA | ASP | 130 | 0.261 |
| CA | THR | 131 | CA | THR | 131 | 0.172 |
| CA | VAL | 132 | CA | VAL | 132 | 0.232 |
| CA | LEU | 133 | CA | LEU | 133 | 0.103 |
| CA | GLU | 134 | CA | GLU | 134 | 0.175 |
| CA | GLU | 135 | CA | GLU | 135 | 0.190 |
| CA | MET | 136 | CA | MET | 136 | 0.220 |
| CA | SER | 137 | CA | SER | 137 | 0.739 |
| CA | LEU | 138 | CA | LEU | 138 | 0.277 |
| CA | PRO | 139 | CA | PRO | 139 | 0.325 |
| CA | GLY | 140 | CA | GLY | 140 | 0.390 |
| CA | ARG | 141 | CA | ARG | 141 | 0.174 |
| CA | TRP | 142 | CA | TRP | 142 | 0.168 |
| CA | LYS | 143 | CA | LYS | 143 | 0.304 |
| CA | PRO | 144 | CA | PRO | 144 | 0.194 |
| CA | LYS | 145 | CA | LYS | 145 | 0.456 |
| CA | MET | 146 | CA | MET | 146 | 0.362 |
| CA | ILE | 147 | CA | ILE | 147 | 0.178 |
| CA | GLY | 148 | CA | GLY | 148 | 0.390 |
| CA | GLY | 149 | CA | GLY | 149 | 0.434 |
| CA | ILE | 150 | CA | ILE | 150 | 0.050 |
| CA | GLY | 151 | CA | GLY | 151 | 0.199 |
| CA | GLY | 152 | CA | GLY | 152 | 0.152 |
| CA | PHE | 153 | CA | PHE | 153 | 0.455 |
| CA | ILE | 154 | CA | ILE | 154 | 0.198 |
| CA | LYS | 155 | CA | LYS | 155 | 0.470 |
| CA | VAL | 156 | CA | VAL | 156 | 0.590 |
| CA | ARG | 157 | CA | ARG | 157 | 0.607 |
| CA | GLN | 158 | CA | GLN | 158 | 0.465 |
| CA | TYR | 159 | CA | TYR | 159 | 0.301 |
| CA | ASP | 160 | CA | ASP | 160 | 0.294 |
| CA | GLN | 161 | CA | GLN | 161 | 0.308 |
| CA | ILE | 162 | CA | ILE | 162 | 0.274 |
| CA | LEU | 163 | CA | LEU | 163 | 0.235 |
| CA | ILE | 164 | CA | ILE | 164 | 0.367 |
| CA | GLU | 165 | CA | GLU | 165 | 0.410 |
| CA | ILE | 166 | CA | ILE | 166 | 0.201 |
| CA | CYS | 167 | CA | CYS | 167 | 0.409 |
| CA | GLY | 168 | CA | GLY | 168 | 0.406 |
| CA | HIS | 169 | CA | HIS | 169 | 0.410 |
| CA | LYS | 170 | CA | LYS | 170 | 0.282 |
| CA | ALA | 171 | CA | ALA | 171 | 0.273 |
| CA | ILE | 172 | CA | ILE | 172 | 0.317 |
| CA | GLY | 173 | CA | GLY | 173 | 0.563 |
| CA | THR | 174 | CA | THR | 174 | 0.129 |
| CA | VAL | 175 | CA | VAL | 175 | 0.237 |
| CA | LEU | 176 | CA | LEU | 176 | 0.155 |
| CA | VAL | 177 | CA | VAL | 177 | 0.240 |
| CA | GLY | 178 | CA | GLY | 178 | 0.386 |
| CA | PRO | 179 | CA | PRO | 179 | 0.340 |
| CA | THR | 180 | CA | THR | 180 | 0.335 |
| CA | PRO | 181 | CA | PRO | 181 | 0.446 |
| CA | VAL | 182 | CA | PHE | 182 | 0.343 |
| CA | ASN | 183 | CA | ASN | 183 | 0.205 |
| CA | ILE | 184 | CA | VAL | 184 | 0.262 |
| CA | ILE | 185 | CA | ILE | 185 | 0.096 |
| CA | GLY | 186 | CA | GLY | 186 | 0.118 |
| CA | ARG | 187 | CA | ARG | 187 | 0.202 |
| CA | ASN | 188 | CA | ASN | 188 | 0.073 |
| CA | LEU | 189 | CA | LEU | 189 | 0.108 |

TABLE 4-continued

Distances between equivalent Cα atoms

| Molecule 1 | | | Molecule 2 | | | distance [Å] |
|---|---|---|---|---|---|---|
| CA | LEU | 190 | CA | LEU | 190 | 0.127 |
| CA | THR | 191 | CA | THR | 191 | 0.177 |
| CA | GLN | 192 | CA | GLN | 192 | 0.175 |
| CA | ILE | 193 | CA | ILE | 193 | 0.241 |
| CA | GLY | 194 | CA | GLY | 194 | 0.118 |
| CA | CYS | 195 | CA | CYS | 195 | 0.375 |
| CA | THR | 196 | CA | THR | 196 | 0.437 |
| CA | LEU | 197 | CA | LEU | 197 | 0.167 |
| CA | ASH | 198 | CA | ASN | 198 | 0.178 |

Molecule 1: HIV-1 PR wt: 1
Molecule 2: HIV-1 PR V82F/I84V mutant:1

Table 4 shows that the I84V, V82F mutations induce structural changes relative to the wild type structure in some parts of the enzyme, but that other regions are less affected. The regions of the protein structure which are not significantly affected by the amino acid mutations are defined as structurally conserved regions. In the present example, the mutations result in localized structural changes in the backbone of HIV protease over a wide range, from 0.038–0.774 Å.

The distances between the polar atoms of the inhibitor shown in FIG. 1 to polar atoms of the wild type and mutant protein, that is hydrogen-bond donors and acceptors, were computed and they are displayed in Table 5.

TABLE 5

Distances between polar atoms of the inhibitor and polar atoms of the protein

| | HIV PR wt: 1 | V82F/I84V: 1 |
|---|---|---|
| O2-Wat301 | 2.92 | 2.89 |
| N1-O27 | 3.36 | 3.46 |
| O6-N30 | 3.30 | 3.61 |
| O6-N29 | 3.19 | 3.55 |
| O7-N29 | 2.84 | 2.87 |
| O7-OD1 29 | 3.42 | 3.54 |
| O7-O1 | 3.31 | 3.19 |
| O3-OD 25 (out) | 2.50 | 2.94 |
| O3-OD 25 (in) | 2.65 | 2.67 |
| O3-OD125 (out) | 3.27 | 3.21 |
| O3-OD125 (in) | 2.80 | 2.67 |
| O5-Wat301 | 2.70 | 2.79 |
| O8-N130 | 3.16 | 2.96 |

Table 5 shows that the polar atoms of the inhibitor interact with the same polar atoms of the two different proteins, in this case the wild type and V82F/I84V mutant HIV proteases. From Table 5, it can be seen that the polar atoms of the enzymes with which the inhibitor interacts belong to the structurally conserved regions. The effects of mutations on the protein-inhibitor interactions can be quantified in terms of the distances between interacting pairs of polar atoms from the inhibitor and from polar atoms of the three-dimensionally conserved substructure of the protein. These distances are similar in the wild type and in the mutant complexes; the average of their differences is only 0.07 Å. The range of the differences is 0.02–0.36 Å.

Example 3

This example illustrates the method by which experimentally-determined crystal structures of two different inhibitors in complexes with wild type HIV protease can be compared and analyzed for the existence of a three-dimensionally conserved substructure. The structures of wild type HIV-1 protease in complexes with inhibitor 1 and with Amprenavir (inhibitor 2) were analyzed by means of (a) an overall superposition of the protein structures; and (b) a study of the distances from polar atoms of the inhibitors to polar atoms of the protein.

The superposition of the protein structures is performed in a two step process: 1) the distance between all pairs of corresponding Cα atoms (Cα atom of residue number 1 in one protein to Cα atom of residue number 1 in the second protein; Cα atom of residue number 2 in one protein to Cα atom of residue number 2 in the second protein; and so on) of the polypeptide chains is minimized by means of a least-square algorithm; 2) the superposition is refined by minimizing, in an iterative process, the distances between corresponding Cα atoms that are closer than a given distance (0.25 Å in this example), thus eliminating regions of the structures having large conformational differences to compute the superposition parameters. The distances between equivalenced Cα atoms after the minimization procedure are shown in Table 6.

TABLE 6

Distances between equivalent Cα atoms

| Molecule 1 | | | Molecule 2 | | | distance [Å] |
|---|---|---|---|---|---|---|
| CA | PRO | 1 | CA | PRO | 1 | 0.200 |
| CA | GLN | 2 | CA | GLN | 2 | 0.320 |
| CA | ILE | 3 | CA | ILE | 3 | 0.147 |
| CA | THR | 4 | CA | THR | 4 | 0.405 |
| CA | LEU | 5 | CA | LEU | 5 | 0.225 |
| CA | TRP | 6 | CA | TRP | 6 | 0.296 |
| CA | GLN | 7 | CA | GLN | 7 | 0.317 |
| CA | ARG | 8 | CA | ARG | 8 | 0.154 |
| CA | PRO | 9 | CA | PRO | 9 | 0.143 |
| CA | LEU | 10 | CA | LEU | 10 | 0.259 |
| CA | VAL | 11 | CA | VAL | 11 | 0.275 |
| CA | THR | 12 | CA | THR | 12 | 0.307 |
| CA | ILE | 13 | CA | ILE | 13 | 0.207 |
| CA | LYS | 14 | CA | LYS | 14 | 0.273 |
| CA | ILE | 15 | CA | ILE | 15 | 0.434 |
| CA | GLY | 16 | CA | GLY | 16 | 0.469 |
| CA | GLY | 17 | CA | GLY | 17 | 0.414 |
| CA | GLN | 18 | CA | GLN | 18 | 0.319 |

TABLE 6-continued

Distances between equivalent Cα atoms

| Molecule 1 | | | Molecule 2 | | | distance [Å] |
|---|---|---|---|---|---|---|
| CA | LEU | 19 | CA | LEU | 19 | 0.161 |
| CA | LYS | 20 | CA | LYS | 20 | 0.155 |
| CA | GLU | 21 | CA | GLU | 21 | 0.196 |
| CA | ALA | 22 | CA | ALA | 22 | 0.338 |
| CA | LEU | 23 | CA | LEU | 23 | 0.246 |
| CA | LEU | 24 | CA | LEU | 24 | 0.292 |
| CA | ASP | 25 | CA | ASP | 25 | 0.142 |
| CA | THR | 26 | CA | THR | 26 | 0.109 |
| CA | GLY | 27 | CA | GLY | 27 | 0.176 |
| CA | ALA | 28 | CA | ALA | 28 | 0.193 |
| CA | ASP | 29 | CA | ASP | 29 | 0.087 |
| CA | ASP | 30 | CA | ASP | 30 | 0.118 |
| CA | THR | 31 | CA | THR | 31 | 0.111 |
| CA | VAL | 32 | CA | VAL | 32 | 0.087 |
| CA | LEU | 33 | CA | LEU | 33 | 0.306 |
| CA | GLU | 34 | CA | GLU | 34 | 0.333 |
| CA | GLU | 35 | CA | GLU | 35 | 0.399 |
| CA | MET | 36 | CA | MET | 36 | 0.296 |
| CA | SER | 37 | CA | SER | 37 | 0.454 |
| CA | LEU | 38 | CA | LEU | 38 | 0.451 |
| CA | PRO | 39 | CA | PRO | 39 | 0.397 |
| CA | GLY | 40 | CA | GLY | 40 | 0.444 |
| CA | ARG | 41 | CA | ARG | 41 | 0.535 |
| CA | TRP | 42 | CA | TRP | 42 | 0.346 |
| CA | LYS | 43 | CA | LYS | 43 | 0.442 |
| CA | PRO | 44 | CA | PRO | 44 | 0.548 |
| CA | LYS | 45 | CA | LYS | 45 | 0.307 |
| CA | MET | 46 | CA | MET | 46 | 0.320 |
| CA | ILE | 47 | CA | ILE | 47 | 0.403 |
| CA | GLY | 48 | CA | GLY | 48 | 0.237 |
| CA | GLY | 49 | CA | GLY | 49 | 0.280 |
| CA | ILE | 50 | CA | ILE | 50 | 0.206 |
| CA | GLY | 51 | CA | GLY | 51 | 0.368 |
| CA | GLY | 52 | CA | GLY | 52 | 0.315 |
| CA | PHE | 53 | CA | PHE | 53 | 0.378 |
| CA | ILE | 54 | CA | ILE | 54 | 0.180 |
| CA | LYS | 55 | CA | LYS | 55 | 0.149 |
| CA | VAL | 56 | CA | VAL | 56 | 0.302 |
| CA | ARG | 57 | CA | ARG | 57 | 0.098 |
| CA | GLN | 58 | CA | GLN | 58 | 0.219 |
| CA | TYR | 59 | CA | TYR | 59 | 0.279 |
| CA | ASP | 60 | CA | ASP | 60 | 0.385 |
| CA | GLN | 61 | CA | GLN | 61 | 0.431 |
| CA | ILE | 62 | CA | ILE | 62 | 0.343 |
| CA | LEU | 63 | CA | LEU | 63 | 0.473 |
| CA | ILE | 64 | CA | ILE | 64 | 0.344 |
| CA | GLU | 65 | CA | GLU | 65 | 0.456 |
| CA | ILE | 66 | CA | ILE | 66 | 0.481 |
| CA | CYS | 67 | CA | CYS | 67 | 0.920 |
| CA | GLY | 68 | CA | GLY | 68 | 0.999 |
| CA | HIS | 69 | CA | HIS | 69 | 0.295 |
| CA | LYS | 70 | CA | LYS | 70 | 0.406 |
| CA | ALA | 71 | CA | ALA | 71 | 0.446 |
| CA | ILE | 72 | CA | ILE | 72 | 0.374 |
| CA | GLY | 73 | CA | GLY | 73 | 0.259 |
| CA | THR | 74 | CA | THR | 74 | 0.276 |
| CA | VAL | 75 | CA | VAL | 75 | 0.165 |
| CA | LEU | 76 | CA | LEU | 76 | 0.220 |
| CA | VAL | 77 | CA | VAL | 77 | 0.202 |
| CA | GLY | 78 | CA | GLY | 78 | 0.231 |
| CA | PRO | 79 | CA | PRO | 79 | 0.131 |
| CA | THR | 80 | CA | THR | 80 | 0.374 |
| CA | PRO | 81 | CA | PRO | 81 | 0.472 |
| CA | VAL | 82 | CA | VAL | 82 | 0.554 |
| CA | ASN | 83 | CA | ASN | 83 | 0.149 |
| CA | ILE | 84 | CA | ILE | 84 | 0.261 |
| CA | ILE | 85 | CA | ILE | 85 | 0.223 |
| CA | GLY | 86 | CA | GLY | 86 | 0.130 |
| CA | ARG | 87 | CA | ARG | 87 | 0.165 |
| CA | ASN | 88 | CA | ASN | 88 | 0.103 |
| CA | LEU | 89 | CA | LEU | 89 | 0.072 |
| CA | LEU | 90 | CA | LEU | 90 | 0.076 |
| CA | THR | 91 | CA | THR | 91 | 0.114 |
| CA | GLN | 92 | CA | GLN | 92 | 0.115 |
| CA | ILE | 93 | CA | ILE | 93 | 0.204 |

TABLE 6-continued

Distances between equivalent Cα atoms

| Molecule 1 | Molecule 2 | distance [Å] |
|---|---|---|
| CA GLY 94 | CA GLY 94 | 0.220 |
| CA CYS 95 | CA CYS 95 | 0.068 |
| CA THR 96 | CA THR 96 | 0.185 |
| CA LEU 97 | CA LEU 97 | 0.095 |
| CA ASN 98 | CA ASN 98 | 0.311 |
| CA PHE 99 | CA PHE 99 | 0.216 |
| CA PRO 101 | CA PRO 1 | 0.455 |
| CA GLN 102 | CA GLN 2 | 0.121 |
| CA ILE 103 | CA ILE 3 | 0.120 |
| CA THR 104 | CA THR 4 | 0.109 |
| CA LEU 105 | CA LEU 5 | 0.128 |
| CA TRP 106 | CA TRP 6 | 0.205 |
| CA GLN 107 | CA GLN 7 | 0.229 |
| CA ARG 108 | CA ARG 8 | 0.211 |
| CA PRO 109 | CA PRO 9 | 0.195 |
| CA LEU 110 | CA LEU 10 | 0.135 |
| CA VAL 111 | CA VAL 11 | 0.086 |
| CA THR 112 | CA THR 12 | 0.166 |
| CA ILE 113 | CA ILE 13 | 0.199 |
| CA LYS 114 | CA LYS 14 | 0.333 |
| CA ILE 115 | CA ILE 15 | 0.356 |
| CA GLY 116 | CA GLY 16 | 0.671 |
| CA GLY 117 | CA GLY 17 | 0.709 |
| CA GLN 118 | CA GLN 18 | 0.370 |
| CA LEU 119 | CA LEU 19 | 0.258 |
| CA LYS 120 | CA LYS 20 | 0.156 |
| CA GLU 121 | CA GLU 21 | 0.250 |
| CA ALA 122 | CA ALA 22 | 0.276 |
| CA LEU 123 | CA LEU 23 | 0.103 |
| CA LEU 124 | CA LEU 24 | 0.112 |
| CA ASP 125 | CA ASP 25 | 0.078 |
| CA THR 126 | CA THR 26 | 0.057 |
| CA GLY 127 | CA GLY 27 | 0.121 |
| CA ALA 128 | CA ALA 28 | 0.098 |
| CA ASP 129 | CA ASP 29 | 0.190 |
| CA ASP 130 | CA ASP 30 | 0.302 |
| CA THR 131 | CA THR 31 | 0.073 |
| CA VAL 132 | CA VAL 32 | 0.178 |
| CA LEU 133 | CA LEU 33 | 0.147 |
| CA GLU 134 | CA GLU 34 | 0.239 |
| CA GLU 135 | CA GLU 35 | 0.101 |
| CA MET 136 | CA MET 36 | 0.235 |
| CA SER 137 | CA SER 37 | 0.391 |
| CA LEU 138 | CA LEU 38 | 0.364 |
| CA PRO 139 | CA PRO 39 | 0.532 |
| CA GLY 140 | CA GLY 40 | 0.213 |
| CA ARG 141 | CA ARG 41 | 0.448 |
| CA TRP 142 | CA TRP 42 | 0.133 |
| CA LYS 143 | CA LYS 43 | 0.195 |
| CA PRO 144 | CA PRO 44 | 0.082 |
| CA LYS 145 | CA LYS 45 | 0.359 |
| CA MET 146 | CA MET 46 | 0.306 |
| CA ILE 147 | CA ILE 47 | 0.076 |
| CA GLY 148 | CA GLY 48 | 0.214 |
| CA GLY 149 | CA GLY 49 | 0.205 |
| CA ILE 150 | CA ILE 50 | 0.163 |
| CA GLY 151 | CA GLY 51 | 0.287 |
| CA GLY 152 | CA GLY 52 | 0.318 |
| CA PHE 153 | CA PHE 53 | 0.125 |
| CA ILE 154 | CA ILE 54 | 0.189 |
| CA LYS 155 | CA LYS 55 | 0.384 |
| CA VAL 156 | CA VAL 56 | 0.510 |
| CA ARG 157 | CA ARG 57 | 0.405 |
| CA GLN 158 | CA GLN 58 | 0.139 |
| CA TYR 159 | CA TYR 59 | 0.361 |
| CA ASP 160 | CA ASP 60 | 0.252 |
| CA GLN 161 | CA GLN 61 | 0.414 |
| CA ILE 162 | CA ILE 62 | 0.337 |
| CA LEU 163 | CA LEU 63 | 0.202 |
| CA ILE 164 | CA ILE 64 | 0.359 |
| CA GLU 165 | CA GLU 65 | 0.463 |
| CA ILE 166 | CA ILE 66 | 0.347 |
| CA CYS 167 | CA CYS 67 | 0.256 |
| CA GLY 168 | CA GLY 68 | 0.471 |
| CA HIS 169 | CA HIS 69 | 0.658 |

TABLE 6-continued

Distances between equivalent Cα atoms

| Molecule 1 | | | Molecule 2 | | | distance [Å] |
|---|---|---|---|---|---|---|
| CA | LYS | 170 | CA | LYS | 70 | 0.489 |
| CA | ALA | 171 | CA | ALA | 71 | 0.445 |
| CA | ILE | 172 | CA | ILE | 72 | 0.396 |
| CA | GLY | 173 | CA | GLY | 73 | 0.523 |
| CA | THR | 174 | CA | THR | 74 | 0.130 |
| CA | VAL | 175 | CA | VAL | 75 | 0.156 |
| CA | LEU | 176 | CA | LEU | 76 | 0.077 |
| CA | VAL | 177 | CA | VAL | 77 | 0.129 |
| CA | GLY | 178 | CA | GLY | 78 | 0.276 |
| CA | PRO | 179 | CA | PRO | 79 | 0.272 |
| CA | THR | 180 | CA | THR | 80 | 0.580 |
| CA | PRO | 181 | CA | PRO | 81 | 0.436 |
| CA | VAL | 182 | CA | VAL | 82 | 0.328 |
| CA | ASN | 183 | CA | ASN | 83 | 0.180 |
| CA | ILE | 184 | CA | ILE | 84 | 0.151 |
| CA | ILE | 185 | CA | ILE | 85 | 0.104 |
| CA | GLY | 186 | CA | GLY | 86 | 0.059 |
| CA | ARG | 187 | CA | ARG | 87 | 0.058 |
| CA | ASH | 188 | CA | ASH | 88 | 0.183 |
| CA | LEU | 189 | CA | LEU | 89 | 0.164 |
| CA | LEU | 190 | CA | LEU | 90 | 0.051 |
| CA | THR | 191 | CA | THR | 91 | 0.216 |
| CA | GLN | 192 | CA | GLN | 92 | 0.162 |
| CA | ILE | 193 | CA | ILE | 93 | 0.158 |
| CA | GLY | 194 | CA | GLY | 94 | 0.047 |
| CA | CYS | 195 | CA | CYS | 95 | 0.050 |
| CA | THR | 196 | CA | THR | 96 | 0.200 |
| CA | LEU | 197 | CA | LEU | 97 | 0.165 |
| CA | ASH | 198 | CA | ASH | 98 | 0.074 |

Molecule 1: HIV-1 PR wt: 1
Molecule 2: HTV-1 PR wt: 2

The distances between the polar atoms of the inhibitors 1 (FIG. 1) and 2 to polar atoms of the protein, that is, hydrogen-bond donors and acceptors, were computed and are shown in Table 7.

TABLE 7

Distances between polar atoms of inhibitors and polar atoms of the proteins

| | Wt: 1 complex | Wt: 2 complex |
|---|---|---|
| O2-Wat301 | 2.92 | 3.02 |
| N1-O27 | 3.36 | 3.58 |
| O6-N30 | 3.30 | 3.50 |
| O6-N29 | 3.19 | 3.51 |
| O7-N29 | 2.84 | — |
| O7-OD1 29 | 3.42 | — |
| O7-O1 | 3.31 | — |
| O3-OD 25 (out) A | 2.50 | 2.80 |
| O3-OD 25 (in) A | 2.65 | 2.66 |
| O3-OD 25 (out) B | 3.27 | 3.07 |
| O3-OD 25 (in) B | 2.80 | 2.68 |
| O5-Wat301 | 2.70 | 2.77 |
| O8-N 30 | 3.16 | — |
| N3-N 30 | | 3.17 |
| N3-OD2 30 | | 3.15 |

Inhibitors 1 (FIG. 1) and 2 (Amprenavir) have similar structural elements, in particular their core, i.e. groups at the P1–P1' positions. However, 2 has a THF group while 1 has a bis-THF group at the P2' position. The P2 groups are identical except for the substitution of an ether oxygen atom in 1 as compared to an amine nitrogen atom at the same position in 2. Table 7 shows that 1 forms more polar interactions with the atoms of the protein that were previously identified as belonging to the structurally conserved substructure than does compound 2. For example, the O7 oxygen atom in compound 1, that forms a polar interaction with N29 nitrogen of the protease, has no counterpart in compound 2. Instead, the O6 oxygen atom of 2 forms longer (and presumably weaker) hydrogen bonds with both N30 (3.50 Å) and N29 (3.51 Å). In contrast, the O6 oxygen of compound 1 forms a shorter (and presumably stronger) hydrogen bond with N29 (3.19 Å). Additionally, as can be seen in Table 7, where both compounds 1 and 2 form interactions with polar atoms in the structurally conserved substructure of HIV protease, the distances between interacting atoms are consistently shorter for compound 1, indicative of presumably stronger binding interactions.

Example 4

Examples 2 and 3 were used to identify a three dimensionally-conserved substructure of HIV protease that is involved in the binding of HIV protease inhibitors and, in particular, to identify polar atoms of these substructural elements that are involved in forming interactions with polar atoms of HIV protease inhibitors. The following two examples demonstrate that a protease inhibitor that contains polar atoms that can make favorable interactions with the polar atoms of the substructure may exhibit resistance-repellent properties.

Compounds 1 and 3 both contain a Bis-THF group at the P2 position that contains two polar atoms, in particular, hydrogen bond acceptor oxygen atoms, that can form hydrogen bonds with the two hydrogen atoms attached to the backbone amide nitrogen atoms on the protein at residues 29 and 30. All three compounds differ in the P2' substituent. Compounds 1 and 3 both are unaffected by the two active site mutations, V82F and I84V, and Ki values for wild type and mutant enzymes are similar for both compounds. In contrast, compound 2, which contains only a single hydrogen bond acceptor atom in the P2 substitutent, is dramatically affected by the active site mutations, which demonstrate high level resistance to 2.

The antiviral activity of compounds 1 and 3 against HIV derived from patient isolates that contain multiple mutations are equivalent to their activity against wild type HIV strains. In contrast, compound 2 is much less effective against the same mutant viruses. None of the patients from whom virus was isolated had ever been exposed to any of the compounds tested herein. Nonetheless, compound 2 exhibited cross resistance to these virus strains that is typically seen with all clinically useful HIV protease inhibitors—4 (Saquinavir), 5 (Ritonavir), 6 (Indinavir) and 7 (Nelfinavir). Compounds 2, 4, 5, 6, and 7 have very different chemical structures, but nonetheless behave as a single class with respect to their antiviral behavior against wild type and multidrug resistant HIV strains. All compounds are dramatically less potent against the multidrug resistant strains of HIV.

In sharp contrast, compounds 1 and 3, which closely resemble each other as well as compound 2, exhibit resistance-repellent behavior in that they are equally effective against wild type and mutant HIV strains that exhibit high level multidrug resistance towards compounds 2, 4, 5, 6, and 7. The resistance-repellent activity of compound 1 was completely unexpected and contrasts with the common and typical loss of antiviral potency experienced with compounds like 2, 4, 5, 6, 7, and indeed most other HIV protease inhibitors represented as similar or different structures that have been reported.

The development and application of the 3D motif method described above successfully revealed the presence of a unique, three dimensionally-conserved substructure of HIV protease that is useful in the design of resistance-repellent inhibitors. Based on this method, compound 3 was predicted, on the basis of comparative molecular modeling using the coordinates of the complexes of compound 1 with wild type and V82F/I84V mutant HIV proteases, to be able to make the same key polar interaction as compound 1 and thereby to exhibit resistance-repellent properties. Based on these data, it is feasible to design protease inhibitors that are predicted to have resistance-repellent properties, and are predicted to be useful for the treatment of both wild type (first line therapy) and drug resistant (salvage therapy) HIV infections.

Any reference to any of the instant compounds also includes a reference to a pharmaceutically acceptable salts thereof.

Any reference to any of the instant compounds also includes a reference to a stereoisomer thereof.

Other substitutions, modifications, changes and omissions may be made in the design, operating conditions and arrangement of the preferred embodiments without departing from the spirit of the invention as expressed in the appended claims.

Additional advantages, features and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

All of the references cited herein, including patents, patent applications, and publications, are hereby incorporated in their entireties by reference.

The claims below are not restricted to the particular embodiments described above.

What is claimed is:
1. An HIV protease inhibitor represented by a formula:

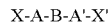

wherein
X is a 5–7 membered non-aromatic monocyclic heterocycle, wherein said heterocycle is fused or bridged with one or more 3–7 membered non-aromatic monocyclic heterocycle to form a polycyclic system, wherein any of said heterocyclic ring systems contains one or more heteroatoms selected from O and S; wherein any sulfur may be optionally substituted by one or two oxygen atoms; and wherein any of said ring systems optionally contains 1 to 6 substituents selected from the group consisting of R2, R3, R5, and R6;
A is OCONH or CONH;
B is

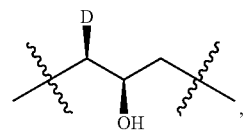

wherein D is aralkyl optionally substituted with one or more groups selected from alkyl, halo, nitro, cyano, $CF_3$, C3–C7 cycloalkyl, C5–C7 cycloalkenyl, R6, OR2, SR2, NHR2, OR3, SR3, NHR3, OR6, SR6, and NHR6;
A' is N(D')E', wherein D' is selected from alkyl, alkenyl, alkynyl, aryl, cycloalkyl, and aralkyl, optionally, substituted by alkyl, halo, nitro, cyano, $CF_3$, O-alkyl, or S-alkyl,
and E' is —$SO_2$—;
X' is

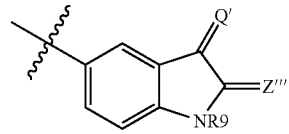

wherein
Z''' is O or NR9
Q' is O, NR9, or CU''U''';
R9 is selected from the group consisting of:
alkyl optionally substituted by R3, R5, R6;
C2–C6 alkenyl, C2–C6 alkynyl, C3–C8 cycloalkyl, and C5–C8 cycloalkenyl, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7;
aryl, wherein said aryl may be optionally substituted with one or more groups selected from the group consisting of aryl, R2, R3, R4, and R6;
C3–C7 cycloalkyl optionally substituted by R2, R3, R5, R6;
$CO_2H$ or R7;
NR3R3, NR6R6, NR7R7, NR3R6, NR6R7, NR3R7, NR2R3, NR2R6, NR2R7, NR2R2;
SO$_n$N(R2)$_2$, SO$_n$N(R3)$_2$, SO$_2$N(R6)$_2$, SO$_n$N(R7)$_2$, SO$_n$NR2R3, SO$_n$NR2R6, SO$_n$NR2R7 SO$_n$NR3R6 SO$_n$NR3R7, SO$_n$NR6R7;
S(O)$_m$R2, S(O)$_m$R3, S(O)$_m$R6, provided R2 is not H; and m is 0, 1 or 2;

U″ and U‴ are each independently
H, OR3, OR6, OR7, OR2;
alkyl substituted by R3, R5, R6;
C2–C6 alkenyl, C2–C6 alkynyl, C3–C8 cycloalkyl, and C5–C8 cycloalkenyl, which groups may be optionally substituted with one or more substituents selected from the group consisting of —OR2, C(O)N(R2)$_2$, S(O)$_n$N(R2)$_2$, CN, SR2, SO$_n$R2, COR2, CO$_2$R2 or NR2C(O)R2, R5, and R7;
aryl, wherein said aryl may be optionally substituted with one or more groups selected from the group consisting of aryl, R2, R3, R4, and R6;
C3–C7 cycloalkyl substituted by R2, R3, R5, R6;
CO$_2$H or R7;
NR3R3, NR6R6, NR7R7, NR3R6, NR6R7, NR3R7, NR2R3, NR2R6, NR2R7, NR2R2;
SO$_n$N(R2)$^2$, SO$_n$N(R3)$_2$, SO$_n$N(R6)$_2$, SO$_n$N(R7)$_2$, SO$_n$NR2R3, SO$_n$NR2R6, SO$_n$NR2R7, SO$_n$NR3R6, SO$_n$NR3R7, SO$_n$NR6R7,
S(O)$_m$R2, S(O)$_m$R3, and S(O)$_m$R6,
provided R2 is not H: and m is 0, 1 or 2; and U″ and U‴ cannot both be H unless one of U and U′ is not H;

R is selected from the group consisting of H, alkyl, aryl, alkenyl,alkynyl, cycloalkyl, and cycloalkenyl, optionally substituted by halo, hydroxy, alkoxy, aryloxy, cycloalkoxy, cyano, nitro, alkylthio, arylthio, cycloalkylthio, amino, or mono- or dialkylamino, mono- or diarylamino, mono- or di-cycloalkylamino, alkanoyl, cycloalkanoyl, aroyl, carboxamido, mono- or dialkylcarboxamido, mono- or diarylcarboxainido, sulfonamido, mono- or dialkylsulfonamido, mono- or diarylsulfonamido, alkylsulfinyl, alkylsulfonyl, arylsulfinyl, arylsulfonyl, cycloalkylsulfinyl, and cycloalkylsulfonyl;

R2 is H or C1–C6 alkyl; optionally substituted by C2–C6 alkenyl, C2–C6 alkynyl, C3–C8 cycloalkyl, or C5–C8 cycloalkenyl; which groups may be optionally substituted with one or more substituents selected from the group consisting of halo, OR, ROH, R-halo, NO2, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, NRPO$_n$OR, oxo, =N—OR, =N—N(R)$_2$, =NR, =NNRC(O)N(R)$_2$, =NNRCO$_n$R, =NNRS(O)$_n$N(R)$_2$, and =NNRS(O)$_n$(R);

or R2 is C1–C6 alkyl; substituted by aryl; which groups may be optionally substituted with one or more substituents selected from the group consisting of halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R)CO$_n$R, NRS(O)$_n$R, NRC[=N(R)]N(R)$_2$, N(R)N(R)CO$_n$R, NRPO$_n$N(R)$_2$, and NRPO$_n$OR; or R2 is C1–C6 alkyl; optionally substituted by halo, OR, ROH, R-halo, NO$_2$, CN, CO$_n$R, CON(R)$_2$, C(S)R, C(S)N(R)$_2$, SO$_n$N(R)$_2$, SR, SO$_n$R, N(R)$_2$, N(R) CO$_n$R, NRS(O)$_n$R, NRC[=N(R)]N(R)$_2$, N(R)N(R) CO$_n$R, NRPO$_n$N(R)$_2$, NRPO$_n$OR, oxo, =N—OR, =N—N(R)$_2$, =NR, =NNRC(O)N(R)$_2$, =NNRCOnR, =NNRS(O)nN(R)$_2$, or =NNRS(O)n(R);

R3 is selected from the grouy consisting of C2–C6 alkenyl, C2–C6 alkynyl, C3–C8 cycloalkyl, and C5–C8 cycloalkenyl; which groups may be optionally substituted with one or more substituents selected from the group consisting of halo, OR2, R2—OH, R2-halo, NO$_2$, CN, CO$_n$R2, C(O)N(R2)$^2$, C(O)N(R2)N(R2)$_2$, C(S)R2, C(S)N(R2)$_2$, S(O)nN(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2)CO$_n$R2, NR2PO$_n$N(R2)$_2$, NR2PO$_n$OR2, oxo, =N—OR2, =N—N(R2)$_2$, =NR2, =NNRC(O)N(R2)$_2$, =NNR2C(O)$_n$R2, =NNR2S(O)$_n$N(R2)$_2$, and =NNR2S(O)$_n$(R2);

R4 is selected from the group consisting of halo, OR8, R2—OH, R3—OH, R2-halo, R3-halo, NO$_2$, CN, CO$_n$R8, CO$_n$R8, CON(R8)$_2$, C(O)N(R8)N(R8)$_2$, C(S)R8, C(S)N(R8)$_2$, SOnN(R8)$_2$, SR8, SO$_n$R8, N(R8)$_2$, N(R8)CO$_n$R8, NR8S(O)$_n$R8, NR8C[=N(R8)]N(R8)$_2$, N(R8)N(R8)CO$_n$R8, NR8PO$_n$N(R8)$_2$ NR8PO$_n$OR8, OC(O)R2, OC(S)R8, OC(O)N(R8)$_2$, OC(S)N(R8)$_2$, and OPO$_n$(R8)$_2$;

R5 is selected from the group consisting of OR8, N(R8)$_2$, NHOH, N(R8)COR8, NR8S(O)$_n$R8, NR8C[=N(R8)]N(R8)$_2$, N(R8)N(R8)C(O)R8, NR8PO$_n$N(R8)$_2$, NR8PO$_n$OR8, R2OH, R3—OH, R2-halo, R3-halo, CN, CO$_n$R8; provided that when n=2, R8 is not H; CON(R8)$_2$, C(O)N(R8)N(R8)$_2$, C(S)$_n$R8, C(S)N(R8)$_2$, S(O)$_n$R8, SO$_n$N(R8)$_2$, halo, NO$_2$, SR8, oxo, =N—OH, =N—OR8, =N—N(R8)$_2$, =NR8, =NNR8C(O)N(R8)$_2$, =NNR8C(O)$_n$R8, =NNR8S(O)$_n$N(R8)$_2$, =NNR8S(O)$_n$(R8), and R3

R6 is aryl wherein said aryl may be optionally substituted with one or more groups selected from aryl, R2, R3, halo, OR2, R2OH, R2-halo, NO$_2$, CN, CO$_n$R2, C(O)N(R2)$_2$, C(O)N(R2)N(R2)$_2$, C(S)R2, C(S)N(R2)$_2$, S(O)$_n$N(R2)$_2$, SR2, SO$_n$R2, N(R)$_2$, N(R2)CO$_n$R2, NR2S(O)$_n$R2, NR2C[=N(R2)]N(R2)$_2$, N(R2)N(R2) CO$_n$R2, NR2PO$_n$N(R2)$_2$, NR2PO$_n$OR2, OC(O)R2, OC(S)R2, OC(O)N(R2)$_2$, OC(S)N(R2)$_2$, and OPO$_n$(R2)$_2$ R7 is selected from the group consisting of C(O)$_n$R8; provided that when n=2; R8 is not H; C(S)R8, C(O)N(R8)$_2$, C(S)N(R8)$_2$, S(O)$_n$R8, and S(O)nN(R8)$_2$;

R8 is R2, R3, or R6;

each n is independently 1 or 2;

its stercoisomeric forms; and its pharmacologically acceptable salts.

2. The compound according to claim 1, wherein X is

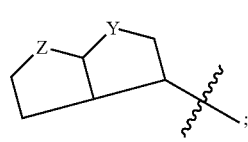

Y is O, or S;
Z is O, or S; and
wherein any ring carbon is optionally substituted by R2, R3, R5, or R6.

3. The compound according to claim 1, wherein X is

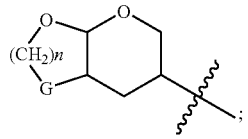

wherein
G is C, O, or S;
n is an integer between 1–2; and
wherein any ring carbon is optionally substituted by R2, R3, R5, or R6.

4. The compound according to claim 1, wherein
X is

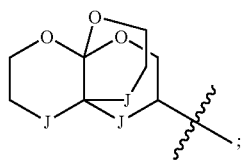

wherein

J is independently CH$_2$, or O, and wherein any ring carbon is optionally substituted by R2, R3, R5, or R6.

5. The compound according to claim 1, wherein:
X is

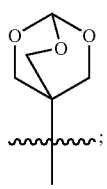

wherein any ring carbon is optionally substituted by R2, R3, R5, or R6.

6. The compound according to claim 1, wherein
X is

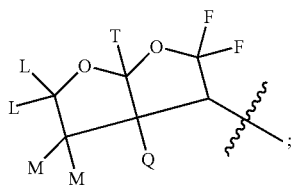

wherein each L is independently H, lower alkyl, oxo, or L forms a carbocyclic or heterocyclic ring with M;

each M is independently H, OH, chloro, fluoro, or M forms a carbocyclic or heterocyclic ring with Q, provided that if one M is OH, the other M is not OH;

Q is H, OH, amino, lower alkyl, alkylamino, alkoxy, halo, or forms a 3–7-membered carbocyclic or heterocyclic ring together with T;

each F is independently H, OH, lower alkyl, halo, or spirocylopropyl, provided that if one R is OH, the other R is not OH;

T is H or F, or T forms a carbocyclic or heterocyclic ring together with F.

7. The HIV protease inhibitor according to claim 1, wherein
X is tetrahydrofurodihydrofuranyl, tetrahydrofurotetrahydrofuranyl, tetrahydropyranotetrahydrofuranyl or tetrahydropyranodihydrofliranyl;
A is OCONH;

B is

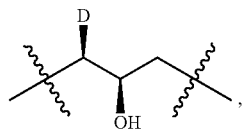

wherein D is aralkyl optionally substituted with one or more groups selected from alkyl, halo, nitro, cyano, CF$_3$, C3–C7 cycloalkyl, C5–C7 cycloalkenyl, R6, OR2, SR2, NHR2, OR3, SR3, NHR3, OR6, SR6 and NHR6; and A' is N(D')E', wherein D' is alkyl, alkenyl, alkynyl aryl, cycloalkyl, or aralkyl optionally substituted by alkyl, halo, or CF$_3$, and E' is —SO$_2$—.

8. The HIV protease inhibitor according to claim 1, wherein:
X is tetrahydrofurotetrahydrofuranyl;
A is OCONH;
B is

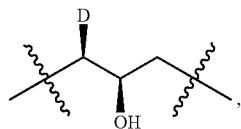

wherein D is benzyl; and
A' is N(D')E', wherein D' is isobutyl and E' is —SO$_2$—.

9. The HIV protease inhibitor according to claim 1, wherein:
X is

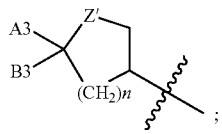

wherein
A3 is H, F or alkoxy;
B3 is F, alkoxy, lower alkyl, or A3 and B3 can form a 3–7 membered heterocyclic ring;
Z' is O, or S; and
n is an integer between 1–3.

10. A compound according to claim 1, bound in a complex with wild type or drug resistant mutant forms of HIV-1 protease.

11. A pharmaceutical composition comprising an effective amount of an inhibitor according to claim 1 and a pharmaceutically acceptable additive, excipient, or diluent.

12. A pharmaceutical composition comprising an effective amount inhibitor according to claim 1 and another antiretroviral agent.

13. A pharmaceutical composition comprising an effective amount of an inhibitor according to claim 1 and a second HIV inhibitor.

14. A pharmaceutical composition comprising an inhibitor according to claim 1 and an additional HIV protease inhibitor.

15. A pharmaceutical composition comprising an effective amount of an inhibitor according to claim 1 and an HIV reverse transcriptase inhibitor.

16. A method of treating a patient suffering from HIV infection, comprising administering to said patient a composition according to claim 1.

17. A method of treatment according to claim 16 wherein said patient is suffering from a multi-drug resistant HIV infection.

18. An HIV protease inhibitor according to claim 1

$$X\text{-}A\text{-}B\text{-}A'\text{-}X' \qquad \text{I}$$

wherein X comprises first and second hydrogen bond acceptor atoms $H_{A1}{:}X$ and $H_{A2}{:}X$, wherein $H_{A1}{:}X$ forms a hydrogen bond with N29 of HIV protease and $H_{A2}{:}X$ forms a hydrogen bond with N30 of HIV protease at the relative positions designated in Table 8;

wherein A comprises a hydrogen bond acceptor atom $H_A{:}A$, and a hydrogen bond donor atom $H_D{:}A$, and wherein $H_A{:}A$ forms a hydrogen bond with solvated water301 of said protease at a relative position designated by O301, and HD:A forms a hydrogen bond with the backbone CO atom of residue 27 of said protease at a relative position designated by O27;

wherein B comprises a hydrogen bond donor or acceptor atom $H_{D/A}{:}B$, wherein $H_{D/A}{:}B$ forms a hydrogen bond with either or both carboxylate side chain oxygens of Asp25 and Asp 125 of said protease at relative positions designated by OD1 25, OD2 25, OD1 125, and OD2 125;

wherein A' comprises a hydrogen bond acceptor atom $H_A{:}A'$, wherein $H_A{:}A'$ forms a hydrogen bond with solvated water301 of said protease at a relative position designated by O301; and wherein X' comprises a hydrogen bond acceptor atom $H_A{:}X'$, wherein $H_A{:}X'$ forms a hydrogen bond with backbone NH atoms of residues 129 and/or 130 of said protease at relative positions designated by N129 and/or N130.

19. A compound according to claim 18, bound in a complex with wild type or drug resistant mutant forms of HIV1 protease.

20. A pharmaceutical composition comprising an effective amount of an inhibitor according to claim 18 and a pharmaceutically acceptable additive, excipient, or diluent.

21. A pharmaceutical composition comprising an effective amount inhibitor according to claim 18 and another antiretroviral agent.

22. A pharmaceutical composition comprising an effective amount of an inhibitor according to ciaim 18 and a second HIV inhibitor.

23. A pharmaceutical composition comprising an inhibitor according to claim 18 and an additional HIV protease inhibitor.

24. A pharmaceutical composition comprising an effective amount of an inhibitor according to claim 18 and an HIV reverse transcriptase inhibitor.

25. A method of treating a patient suffering from HIV infection, comprising administering to said patient a composition according to claim 18.

26. A method of treatment according to claim 25 wherein said patient is suffering from a multi-drug resistant HIV infection.

* * * * *